United States Patent
Kimura et al.

(10) Patent No.: US 6,576,441 B1
(45) Date of Patent: Jun. 10, 2003

(54) SEMAPHORIN Z AND GENE ENCODING THE SAME

(75) Inventors: Toru Kimura, Shiga (JP); Kaoru Kikuchi, Hyogo (JP)

(73) Assignee: Sumitomo Pharmaceuticals Company, Limited, Osaka-fu (JP)

( * ) Notice: Subject to any disclaimer, the term of this patent is extended or adjusted under 35 U.S.C. 154(b) by 0 days.

(21) Appl. No.: 09/077,940

(22) PCT Filed: Dec. 2, 1996

(86) PCT No.: PCT/JP96/03517

§ 371 (c)(1),
(2), (4) Date: Jun. 5, 1998

(87) PCT Pub. No.: WO97/20928

PCT Pub. Date: Jun. 12, 1997

(30) Foreign Application Priority Data

Dec. 6, 1995 (JP) .............................. 7-345187
Oct. 31, 1996 (JP) .............................. 8-307205

(51) Int. Cl.[7] .......................... C12P 21/06; C12N 1/20; C12N 15/00; C07H 21/04
(52) U.S. Cl. ................ 435/69.1; 435/320.1; 435/252.3; 536/23.1
(58) Field of Search .............................. 536/23.1–24.5; 514/44; 435/320.1, 325, 252.3, 254.2, 69.1

(56) References Cited

U.S. PATENT DOCUMENTS

| | | | |
|---|---|---|---|
| 5,312,734 A | * | 5/1994 | Uhl et al. |
| 5,416,197 A | | 5/1995 | Raper et al. |
| 5,777,097 A | * | 7/1998 | Lee et al. |
| 5,807,826 A | | 9/1998 | Goodman et al. |
| 5,935,865 A | * | 8/1999 | Goodman et al. |

FOREIGN PATENT DOCUMENTS

| | | |
|---|---|---|
| EP | 0396719 B1 | 11/1990 |
| EP | 0 960 888 A1 | 12/1999 |
| WO | 9417831 | 8/1994 |
| WO | 9507706 | 3/1995 |

OTHER PUBLICATIONS

WO9534651, Lovenberg et al., Dec. 1995.*
Crooke et al, Antisense & Nucl. Acid Drug Dev. 8:115–22, 1998.*
Jenkins et al, PCR Methods and Appl., S77–81, 1994.*
Choh et al, PNAS, 77(6):3211–14, 1980.*
Sambrook et al, Molecular Cloning, 16.1–16.16, 1989.*
Jackowski, British J. of Neurosurgery vol. 9 pp303–317, 1995.*
Skolnick et al., Trends in Biotech 18(1):34–39, 2000.*
Gura et al., Science 270:575–76, 1995.*
Stein et al., 261:1004–1012, 1993.*
Liuzzi et al., Neurosurg. Clinics of N.A., 2(1):31–42, 1991.*
Luo et al., Cell, 75:217–227, 1993.*
Dodd et al., Cell, 81:471–74, 1995.*
Matthes et al., Cell 81:631–639, 1995.*
Jobling et al., Mol. Microbiol., 5(7):1755–67 1991.*
Eide et al., Spinal Cord 36:601–612, 1998.*
Devor et al., J. of the Autonomic NS, 7:371–384, 1983.*
Dray et al., Trends in Pharm. Sci., 15:190–197, 1994.*
Tanelian et al., Nature Medicine, 3:1398–1401, 1997.*
Kikuchi et al., Mol. Br. Res., 51:229–37, 1997.*
Kaoru Kikuchi et al., *Molecular Brain Research*, vol. 51, (1997), pp. 229–237. XP002206715.
NCBI Database Accession No. H45909 (Jul. 31, 1995).
Mark D. Adams et al., *Nature Genetics*, vol. 4, pp. 373–380 (Aug. 1993).
M. E. Schwab et al., *Annu. Rev. Neurosci.*, vol. 16, pp. 565–595 (1993).
Alan R. Johnson, *BioEssays*, vol. 15, No. 12, pp. 807–813 (Dec. 1993).
Yuling Lao et al., *Neuron*, vol. 14, pp. 1131–1140 (Jun. 1995).
Christine E. Bandtlow et al., *Science*, vol. 259, pp. 80–83 (Jan. 1993).
Martin E. Schwab et al., *The Journal of Neuroscience*, vol. 8, No. 7, pp. 2381–2393 (Jul. 1988).
Clifford J. Woolf, *Nature*, vol. 378, pp.439–440 (Nov. 1995).
David J. Matthes et al., *Cell*, vol. 81, pp. 631–639 (May 1995).
Elizabeth K. Messersmith et al., *Neuron*, vol. 14, pp. 949–959 (May 1995).
Alex L. Kolodkin et al., *Cell*, vol. 75, pp. 1389–1399 (Dec. 1993).
Andreas W. Püschel et al., *Neuron*, vol. 14, pp. 941–948 (May 1995).
Jane Dodd et al., *Cell*, vol. 81, pp. 471–474 (May 1995).
Alex L. Kolodkin et al., *Neuron*, vol. 9, pp. 831–845 (Nov. 1992).
Yuling Luo et al., *Cell*, vol. 75, pp. 217–227 (Oct. 1993).
Barbara S. Bregman et al., *Nature*, vol. 378, pp. 498–501 (Nov. 1995).
Lisa Schnell et al., *Nature*, vol. 343, pp. 269–272 (Jan. 1990).
Samuel David et al., *Science*, vol. 214, pp. 931–933 (Nov. 1981).
P.M. Richardson et al., *Nature*, vol. 284, pp. 264–265 (Mar. 1980).

* cited by examiner

*Primary Examiner*—Gary Kunz
*Assistant Examiner*—Sharon Turner
(74) *Attorney, Agent, or Firm*—Birch, Stewart, Kolasch & Birch, LLP

(57) ABSTRACT

Novel semaphorin Z; a gene thereof; a partial peptide of the semaphorin Z; an antibody; a DNA or an RNA complementary to the semaphorin Z gene; a method for screening a semaphorin Z inhibitor by using the semaphorin Z; the semaphorin Z inhibitor obtained by the screening; and a CNS neuron regeneration promoter comprising the inhibitor.

7 Claims, 10 Drawing Sheets

SEQUENCE LISTING

```
<160> NUMBER OF SEQ ID NOS: 20

<210> SEQ ID NO 1
<211> LENGTH: 3692
<212> TYPE: DNA
<213> ORGANISM: Rattus norvegicus
<220> FEATURE:
<221> NAME/KEY: 5'UTR
<222> LOCATION: (1)..(18)
<223> OTHER INFORMATION:
<221> NAME/KEY: CDS
<222> LOCATION: (19)..(2682)
<223> OTHER INFORMATION:
<221> NAME/KEY: 3'UTR
```

<222> LOCATION: (2683)..(3653)
<223> OTHER INFORMATION:
<221> NAME/KEY: polyA_site
<222> LOCATION: (3654)..(3692)
<223> OTHER INFORMATION:

<400> SEQUENCE: 1

```
ggtcacctgg tcctcacc atg tgg acc ccg cga gcg ccc cct cca cgc ccg         51
                    Met Trp Thr Pro Arg Ala Pro Pro Pro Arg Pro
                     1               5                  10 gcc ctg ctg ttc ctc ctg ctg ttg ctg agg gtc acc cat ggc ctt            99
Ala Leu Leu Phe Leu Leu Leu Leu Leu Arg Val Thr His Gly Leu
         15                  20                  25 ttc cca gat gaa cca cct cca ctc agt gtg gct ccc agg gac tac ctg       147
Phe Pro Asp Glu Pro Pro Pro Leu Ser Val Ala Pro Arg Asp Tyr Leu
         30                  35                  40 agc cac tac ccc gtg ttc gtg ggc agc ggg cct ggt cgt ctg acc cct       195
Ser His Tyr Pro Val Phe Val Gly Ser Gly Pro Gly Arg Leu Thr Pro
     45                  50                  55 gca gag ggt gct gag gac ctc aac atc cag aga gtg cta cgt gtt aac       243
Ala Glu Gly Ala Glu Asp Leu Asn Ile Gln Arg Val Leu Arg Val Asn
 60                  65                  70                  75 agg aca ctg ttc atc ggg gac aga gac aac ctg tac caa gta gaa ctg       291
Arg Thr Leu Phe Ile Gly Asp Arg Asp Asn Leu Tyr Gln Val Glu Leu
                 80                  85                  90 gag cca tcc aca tcc acg gag ctg cgg tat cag cgg aag ctt acc tgg       339
Glu Pro Ser Thr Ser Thr Glu Leu Arg Tyr Gln Arg Lys Leu Thr Trp
             95                 100                 105 cgc tcc aac ccc agt gac atc gat gtg tgt cgg atg aag ggc aag caa       387
Arg Ser Asn Pro Ser Asp Ile Asp Val Cys Arg Met Lys Gly Lys Gln
         110                 115                 120 gag ggt gag tgt cgg aac ttt gtc aag gtg ctc ctg ctt cgt gac gaa       435
Glu Gly Glu Cys Arg Asn Phe Val Lys Val Leu Leu Leu Arg Asp Glu
     125                 130                 135 tcc acg ctc ttc gtg tgc ggc tcc aat gca ttc aat ccc atc tgt gcc       483
Ser Thr Leu Phe Val Cys Gly Ser Asn Ala Phe Asn Pro Ile Cys Ala
140                 145                 150                 155 aat tac agt atg gac aca ctg cag ctt ctt gga gac aac atc agt ggt       531
Asn Tyr Ser Met Asp Thr Leu Gln Leu Leu Gly Asp Asn Ile Ser Gly
                 160                 165                 170 atg gcc cgc tgc ccc tac gac ccc aag cat gcc aat gtc gcc ctc ttc       579
Met Ala Arg Cys Pro Tyr Asp Pro Lys His Ala Asn Val Ala Leu Phe
             175                 180                 185 tca gat ggg atg ctc ttc aca gcc aca gta act gac ttc cta gcc atc       627
Ser Asp Gly Met Leu Phe Thr Ala Thr Val Thr Asp Phe Leu Ala Ile
         190                 195                 200 gac gct gtt atc tac cgt agc ctt ggg gac cgg ccc aca ctg cgc aca       675
Asp Ala Val Ile Tyr Arg Ser Leu Gly Asp Arg Pro Thr Leu Arg Thr
     205                 210                 215 gta aag cat gac tcc aag tgg ttt aaa gag cca tac ttt gtg cat gcg       723
Val Lys His Asp Ser Lys Trp Phe Lys Glu Pro Tyr Phe Val His Ala
220                 225                 230                 235 gtg gag tgg gga agc cac gtc tac ttc ttc ttc cgg gag atc gcc atg       771
Val Glu Trp Gly Ser His Val Tyr Phe Phe Phe Arg Glu Ile Ala Met
                 240                 245                 250 gag ttt aac tat ctg gaa aag gtg gtg gtg tcc cgt gtg gcc cgt gta       819
Glu Phe Asn Tyr Leu Glu Lys Val Val Val Ser Arg Val Ala Arg Val
             255                 260                 265 tgc aag aat gat gtg ggc ggc tcc cca cgg gtg ctg gag aag cag tgg       867
Cys Lys Asn Asp Val Gly Gly Ser Pro Arg Val Leu Glu Lys Gln Trp
         270                 275                 280
```

```
act tcc ttc ctg aag gcc cgg ctc aac tgc tcc gtg cct ggg gac tca      915
Thr Ser Phe Leu Lys Ala Arg Leu Asn Cys Ser Val Pro Gly Asp Ser
    285                 290                 295 cac ttc tac ttc aat gta ctg cag gct gtg act ggt gtg gtg agc ctt      963
His Phe Tyr Phe Asn Val Leu Gln Ala Val Thr Gly Val Val Ser Leu
300                 305                 310                 315 ggc ggc cgt cca gtg att ctt gct gtc ttc tca act cct agc aac agc     1011
Gly Gly Arg Pro Val Ile Leu Ala Val Phe Ser Thr Pro Ser Asn Ser
                320                 325                 330 atc cct ggc tca gct gtc tgt gcc ttt gac atg aac caa gtg gct gct     1059
Ile Pro Gly Ser Ala Val Cys Ala Phe Asp Met Asn Gln Val Ala Ala
            335                 340                 345 gtg ttt gaa ggc cgc ttc cgg gag cag aag tca cct gag tca atc tgg     1107
Val Phe Glu Gly Arg Phe Arg Glu Gln Lys Ser Pro Glu Ser Ile Trp
        350                 355                 360 acc cca gtg cct gag gac caa gta cca cgg ccc agg ccc ggg tgc tgt     1155
Thr Pro Val Pro Glu Asp Gln Val Pro Arg Pro Arg Pro Gly Cys Cys
    365                 370                 375 gca gcg ccc ggt atg cag tac aac gca tcc aat gcc ctt cct gac gag     1203
Ala Ala Pro Gly Met Gln Tyr Asn Ala Ser Asn Ala Leu Pro Asp Glu
380                 385                 390                 395 att ctc aac ttt gta aag acc cac cca ctg atg gac gaa gcg gtg ccc     1251
Ile Leu Asn Phe Val Lys Thr His Pro Leu Met Asp Glu Ala Val Pro
                400                 405                 410 tcc ctg ggc cac tcg cct tgg att gtg aga act ctg ata cgg cac cag     1299
Ser Leu Gly His Ser Pro Trp Ile Val Arg Thr Leu Ile Arg His Gln
            415                 420                 425 ctg acc cga gtg gct gtg gat gtg ggt gca ggc cca tgg ggc aat cag     1347
Leu Thr Arg Val Ala Val Asp Val Gly Ala Gly Pro Trp Gly Asn Gln
        430                 435                 440 aca ata gtc ttc ctt ggc tct gag gtt ggc aca gtc ctc aaa ttc ctt     1395
Thr Ile Val Phe Leu Gly Ser Glu Val Gly Thr Val Leu Lys Phe Leu
    445                 450                 455 gtg aag ccc aat gcc agt gtc tca ggg acc aca ggg ccc agc atc ttt     1443
Val Lys Pro Asn Ala Ser Val Ser Gly Thr Thr Gly Pro Ser Ile Phe
460                 465                 470                 475 ttg gag gag ttt gag acc tac cgg cca gac agg tgt gga cga tcc agc     1491
Leu Glu Glu Phe Glu Thr Tyr Arg Pro Asp Arg Cys Gly Arg Ser Ser
                480                 485                 490 agt gct ggt gag tgg gga caa cga ctt ctg agc ctg gag cta gat gct     1539
Ser Ala Gly Glu Trp Gly Gln Arg Leu Leu Ser Leu Glu Leu Asp Ala
            495                 500                 505 gcc tca ggt ggc ctg ctg gca gcc ttc ccc cgc tgt gtg gtt cgt gtt     1587
Ala Ser Gly Gly Leu Leu Ala Ala Phe Pro Arg Cys Val Val Arg Val
        510                 515                 520 cct gtt gcc cgc tgc cag ctg tac tcg ggg tgc atg aag aac tgc att     1635
Pro Val Ala Arg Cys Gln Leu Tyr Ser Gly Cys Met Lys Asn Cys Ile
    525                 530                 535 ggc agc caa gat cca tac tgc ggg tgg gcc ccc gat ggc tcc tgc atc     1683
Gly Ser Gln Asp Pro Tyr Cys Gly Trp Ala Pro Asp Gly Ser Cys Ile
540                 545                 550                 555 ttc ctc aga cca gga acc agt gcc acg ttt gag caa gat gtg tcc ggg     1731
Phe Leu Arg Pro Gly Thr Ser Ala Thr Phe Glu Gln Asp Val Ser Gly
                560                 565                 570 gcc agc acc tct ggc tta ggt gac tgc act gga ctc ttg cgc gcc agc     1779
Ala Ser Thr Ser Gly Leu Gly Asp Cys Thr Gly Leu Leu Arg Ala Ser
            575                 580                 585 ctc tca gat gac cgc gca ggg ctg gta tcg gtg aac ctg ctg gtg acg     1827
Leu Ser Asp Asp Arg Ala Gly Leu Val Ser Val Asn Leu Leu Val Thr
        590                 595                 600
```

```
                                                                -continued tcc tcg gtg gca gcg ttc gtg gtg ggt gcc gtg gtg tcc ggt ttc agc         1875
Ser Ser Val Ala Ala Phe Val Val Gly Ala Val Val Ser Gly Phe Ser
    605                 610                 615 gtg ggc tgg ttc gtg ggt ctc cgc gag cgg cgg gag ctg gcc cgg cgc         1923
Val Gly Trp Phe Val Gly Leu Arg Glu Arg Arg Glu Leu Ala Arg Arg
620                 625                 630                 635 aag gac aag gaa gcc atc ctg gcg cat ggc ggc agc gag gca gtg ctg         1971
Lys Asp Lys Glu Ala Ile Leu Ala His Gly Gly Ser Glu Ala Val Leu
                640                 645                 650 agc gtg agc cga ctg ggc gag cgc agg gga acc ggg act ggg ggt cgt         2019
Ser Val Ser Arg Leu Gly Glu Arg Arg Gly Thr Gly Thr Gly Gly Arg
            655                 660                 665 ggg gga gcc ggc ggc ggt ccc ggg ggt ccc ccg gag gcc ctg ctg gcc         2067
Gly Gly Ala Gly Gly Gly Pro Gly Gly Pro Pro Glu Ala Leu Leu Ala
        670                 675                 680 ccg ctt atg cag aat ggc tgg aca aag gcg gca ctg ctg cat ggt ggt         2115
Pro Leu Met Gln Asn Gly Trp Thr Lys Ala Ala Leu Leu His Gly Gly
    685                 690                 695 cct cac gac ctg gat tcg ggg ctg ctg ccc acc cct gag cag acg cct         2163
Pro His Asp Leu Asp Ser Gly Leu Leu Pro Thr Pro Glu Gln Thr Pro
700                 705                 710                 715 ctg ccc cag aaa cgc ctg ccc aca aca cac cca cac gcc cac gcc cta         2211
Leu Pro Gln Lys Arg Leu Pro Thr Thr His Pro His Ala His Ala Leu
                720                 725                 730 gga ccg cga gcc tgg gac cac agc cac gcg ctg ctg tcg gcc tct gcc         2259
Gly Pro Arg Ala Trp Asp His Ser His Ala Leu Leu Ser Ala Ser Ala
            735                 740                 745 tcc aca tcc ttg ctc ctg ctg gcg cac acc cgc gcc cct gag cag ccc         2307
Ser Thr Ser Leu Leu Leu Leu Ala His Thr Arg Ala Pro Glu Gln Pro
        750                 755                 760 cca gtg ccg act gag tca ggc ccg gaa tct cgc ctc tgc gcc cca aga         2355
Pro Val Pro Thr Glu Ser Gly Pro Glu Ser Arg Leu Cys Ala Pro Arg
    765                 770                 775 tcc tgc cgg gcc tct cac cca ggc gac ttc cca ctc acg cct cac gcc         2403
Ser Cys Arg Ala Ser His Pro Gly Asp Phe Pro Leu Thr Pro His Ala
780                 785                 790                 795 agc ccg gac cgc cgg cgg gtt gtg tcc gca ccc acg ggc ccc ttg gac         2451
Ser Pro Asp Arg Arg Arg Val Val Ser Ala Pro Thr Gly Pro Leu Asp
                800                 805                 810 tct tct tcg gtg ggc gac gac ctt cca ggg cca tgg agc cca cct gca         2499
Ser Ser Ser Val Gly Asp Asp Leu Pro Gly Pro Trp Ser Pro Pro Ala
            815                 820                 825 acc agc agc ctg cgg agg ccg ggc ccc cat ggg ccc cca aca gcc gcc         2547
Thr Ser Ser Leu Arg Arg Pro Gly Pro His Gly Pro Pro Thr Ala Ala
        830                 835                 840 ctg cgg cgc aca cac aca ttc aac agc ggc gag gcg agg ccc ggg ggt         2595
Leu Arg Arg Thr His Thr Phe Asn Ser Gly Glu Ala Arg Pro Gly Gly
    845                 850                 855 cac cgt cct cgc cgc cac gca ccc gcg gac tct aca cac ttg ctg ccc         2643
His Arg Pro Arg Arg His Ala Pro Ala Asp Ser Thr His Leu Leu Pro
860                 865                 870                 875 tgc ggg acg ggc gag cgg act gca ccc ccg gta ccc tag gccgggcgga          2692
Cys Gly Thr Gly Glu Arg Thr Ala Pro Pro Val Pro
                880                 885 tgcctcgacg gtgccaacca cagcgacccg ggcgtcagcc caggtcaccg agccctactg       2752
gcgccgagtg ggacgcgttc gttccccacc ctcgcgggtg gggatctcct cgccacaggg       2812
aagcacaaga gcccctcca tcccggaaga tgcagaacat gaagcccggg ggtgggcggg        2872
aagaggctga ccttttacct gagcatagac tttgatttgt gtttattgtg agtttggttt       2932
```

-continued

```
tttttttttt ctaagaaatt gcacagcccc attcttactt ggggtgtcgg ccggggtggg    2992
aggtgaggat atgggtaac gggaggcaga gctgcagaca cgagccttcc tgcctcaaca    3052
catcctccct agaagggacc ccctccccct tcctgggctc ctgcgcgcgc gcgcgcgcgc    3112
gcgcgtgtgt gtgtgtgtgt gtgtgtgtgt gtccgtgtgc atggcctgtt tgtgtgcaaa    3172
ggcccgaggc agaagtatgt gtgcgtgcgt gtgagacagg gctcccgtgt gtgtgtgtgt    3232
gtgtgtgtgt gtgtgtgtgt gtgtgtgtgt gcgactcaga atgtgggtgg tggtgccctc    3292
agagaccctg gcattggctg agccaatgtt ggtacttctg gaaagaaacc caggggatgg    3352
agcctctgag gtgccggttg gagttcaaat cctgctcctg cagagggaat ctgggggatcc    3412 aggctgggag atgggggaac ctacttctaa agggcttgtg ggggttttg ggagggtgga    3472 agtgggcaga caccccctgta aatacagccc tggggtggtc agagaggccc atgccacctg    3532
tccccacttg tgcatgcccc tctgactgcc aactgaccat gcatgccacg tggccagctg    3592
agtccaggac cctcctcagc cctatccctg tcaataaaac tcttgtttac atccaccgcc    3652 caaaaaaaa aaaaaaaaaa aaaaaaaaaa aaaaaaaaa                            3692
```

<210> SEQ ID NO 2
<211> LENGTH: 887
<212> TYPE: PRT
<213> ORGANISM: Rattus norvegicus

<400> SEQUENCE: 2

```
Met Trp Thr Pro Arg Ala Pro Pro Arg Pro Ala Leu Leu Phe Leu
 1               5                  10                  15

Leu Leu Leu Leu Arg Val Thr His Gly Leu Phe Pro Asp Glu Pro
                20                  25                  30

Pro Pro Leu Ser Val Ala Pro Arg Asp Tyr Leu Ser His Tyr Pro Val
            35                  40                  45

Phe Val Gly Ser Gly Pro Gly Arg Leu Thr Pro Ala Glu Gly Ala Glu
        50                  55                  60

Asp Leu Asn Ile Gln Arg Val Leu Arg Val Asn Arg Thr Leu Phe Ile
 65                  70                  75                  80

Gly Asp Arg Asp Asn Leu Tyr Gln Val Glu Leu Glu Pro Ser Thr Ser
                    85                  90                  95

Thr Glu Leu Arg Tyr Gln Arg Lys Leu Thr Trp Arg Ser Asn Pro Ser
                100                 105                 110

Asp Ile Asp Val Cys Arg Met Lys Gly Lys Gln Glu Gly Glu Cys Arg
            115                 120                 125

Asn Phe Val Lys Val Leu Leu Leu Arg Asp Glu Ser Thr Leu Phe Val
        130                 135                 140

Cys Gly Ser Asn Ala Phe Asn Pro Ile Cys Ala Asn Tyr Ser Met Asp
145                 150                 155                 160

Thr Leu Gln Leu Leu Gly Asp Asn Ile Ser Gly Met Ala Arg Cys Pro
                165                 170                 175

Tyr Asp Pro Lys His Ala Asn Val Ala Leu Phe Ser Asp Gly Met Leu
            180                 185                 190

Phe Thr Ala Thr Val Thr Asp Phe Leu Ala Ile Asp Ala Val Ile Tyr
        195                 200                 205

Arg Ser Leu Gly Asp Arg Pro Thr Leu Arg Thr Val Lys His Asp Ser
    210                 215                 220

Lys Trp Phe Lys Glu Pro Tyr Val His Ala Val Glu Trp Gly Ser
225                 230                 235                 240
```

-continued

```
His Val Tyr Phe Phe Phe Arg Glu Ile Ala Met Glu Phe Asn Tyr Leu
            245                 250                 255

Glu Lys Val Val Val Ser Arg Val Ala Arg Val Cys Lys Asn Asp Val
        260                 265                 270

Gly Gly Ser Pro Arg Val Leu Glu Lys Gln Trp Thr Ser Phe Leu Lys
            275                 280                 285

Ala Arg Leu Asn Cys Ser Val Pro Gly Asp Ser His Phe Tyr Phe Asn
        290                 295                 300

Val Leu Gln Ala Val Thr Gly Val Val Ser Leu Gly Gly Arg Pro Val
305                 310                 315                 320

Ile Leu Ala Val Phe Ser Thr Pro Ser Asn Ser Ile Pro Gly Ser Ala
                325                 330                 335

Val Cys Ala Phe Asp Met Asn Gln Val Ala Ala Val Phe Glu Gly Arg
                340                 345                 350

Phe Arg Glu Gln Lys Ser Pro Glu Ser Ile Trp Thr Pro Val Pro Glu
            355                 360                 365

Asp Gln Val Pro Arg Pro Arg Pro Gly Cys Cys Ala Ala Pro Gly Met
        370                 375                 380

Gln Tyr Asn Ala Ser Asn Ala Leu Pro Asp Glu Ile Leu Asn Phe Val
385                 390                 395                 400

Lys Thr His Pro Leu Met Asp Glu Ala Val Pro Ser Leu Gly His Ser
                405                 410                 415

Pro Trp Ile Val Arg Thr Leu Ile Arg His Gln Leu Thr Arg Val Ala
                420                 425                 430

Val Asp Val Gly Ala Gly Pro Trp Gly Asn Gln Thr Ile Val Phe Leu
            435                 440                 445

Gly Ser Glu Val Gly Thr Val Leu Lys Phe Leu Val Lys Pro Asn Ala
450                 455                 460

Ser Val Ser Gly Thr Thr Gly Pro Ser Ile Phe Leu Glu Glu Phe Glu
465                 470                 475                 480

Thr Tyr Arg Pro Asp Arg Cys Gly Arg Ser Ser Ala Gly Glu Trp
                485                 490                 495

Gly Gln Arg Leu Leu Ser Leu Glu Leu Asp Ala Ala Ser Gly Gly Leu
            500                 505                 510

Leu Ala Ala Phe Pro Arg Cys Val Val Arg Val Pro Val Ala Arg Cys
                515                 520                 525

Gln Leu Tyr Ser Gly Cys Met Lys Asn Cys Ile Gly Ser Gln Asp Pro
            530                 535                 540

Tyr Cys Gly Trp Ala Pro Asp Gly Ser Cys Ile Phe Leu Arg Pro Gly
545                 550                 555                 560

Thr Ser Ala Thr Phe Glu Gln Asp Val Ser Gly Ala Ser Thr Ser Gly
                565                 570                 575

Leu Gly Asp Cys Thr Gly Leu Leu Arg Ala Ser Leu Ser Asp Asp Arg
            580                 585                 590

Ala Gly Leu Val Ser Val Asn Leu Leu Val Thr Ser Ser Val Ala Ala
            595                 600                 605

Phe Val Val Gly Ala Val Val Ser Gly Phe Ser Val Gly Trp Phe Val
            610                 615                 620

Gly Leu Arg Glu Arg Arg Glu Leu Ala Arg Arg Lys Asp Lys Glu Ala
625                 630                 635                 640

Ile Leu Ala His Gly Gly Ser Glu Ala Val Leu Ser Val Ser Arg Leu
                645                 650                 655
```

```
Gly Glu Arg Arg Gly Thr Gly Thr Gly Arg Gly Gly Ala Gly Gly
            660                 665                 670

Gly Pro Gly Gly Pro Pro Glu Ala Leu Leu Ala Pro Leu Met Gln Asn
        675                 680                 685

Gly Trp Thr Lys Ala Ala Leu Leu His Gly Gly Pro His Asp Leu Asp
    690                 695                 700

Ser Gly Leu Leu Pro Thr Pro Glu Gln Thr Pro Leu Pro Gln Lys Arg
705                 710                 715                 720

Leu Pro Thr Thr His Pro His Ala His Ala Leu Gly Pro Arg Ala Trp
                725                 730                 735

Asp His Ser His Ala Leu Leu Ser Ala Ser Ala Ser Thr Ser Leu Leu
            740                 745                 750

Leu Leu Ala His Thr Arg Ala Pro Glu Gln Pro Pro Val Pro Thr Glu
        755                 760                 765

Ser Gly Pro Glu Ser Arg Leu Cys Ala Pro Arg Ser Cys Arg Ala Ser
    770                 775                 780

His Pro Gly Asp Phe Pro Leu Thr Pro His Ala Ser Pro Asp Arg Arg
785                 790                 795                 800

Arg Val Val Ser Ala Pro Thr Gly Pro Leu Asp Ser Ser Val Gly
                805                 810                 815

Asp Asp Leu Pro Gly Pro Trp Ser Pro Ala Thr Ser Ser Leu Arg
            820                 825                 830

Arg Pro Gly Pro His Gly Pro Pro Thr Ala Ala Leu Arg Arg Thr His
        835                 840                 845

Thr Phe Asn Ser Gly Glu Ala Arg Pro Gly Gly His Arg Pro Arg Arg
    850                 855                 860

His Ala Pro Ala Asp Ser Thr His Leu Leu Pro Cys Gly Thr Gly Glu
865                 870                 875                 880

Arg Thr Ala Pro Pro Val Pro
                885

<210> SEQ ID NO 3
<211> LENGTH: 3524
<212> TYPE: DNA
<213> ORGANISM: Homo sapiens
<220> FEATURE:
<221> NAME/KEY: 5'UTR
<222> LOCATION: (1)..(38)
<223> OTHER INFORMATION:
<221> NAME/KEY: 3'UTR
<222> LOCATION: (2706)..(3524)
<223> OTHER INFORMATION:
<221> NAME/KEY: CDS
<222> LOCATION: (39)..(2702)
<223> OTHER INFORMATION:

<400> SEQUENCE: 3
tccgaggcgt cacctcctcc tgtcgcctgg ccctcgcc atg cag acc ccg cga gcg    56
                                           Met Gln Thr Pro Arg Ala
                                             1               5 tcc cct ccc cgc ccg gcc ctg ctg ctt ctg ctg ctg cta ctg ggg ggc   104
Ser Pro Pro Arg Pro Ala Leu Leu Leu Leu Leu Leu Leu Leu Gly Gly
              10                  15                  20 gcc cac ggc ctc ttt cct gag gac ccg ccg ccg ctt agc gtg gcc ccc   152
Ala His Gly Leu Phe Pro Glu Asp Pro Pro Pro Leu Ser Val Ala Pro
         25                  30                  35 agg gac tac ctg aac cac tat ccc gtg ttt gtg ggc agc ggg ccc gga   200
Arg Asp Tyr Leu Asn His Tyr Pro Val Phe Val Gly Ser Gly Pro Gly
     40                  45                  50
```

```
cgc ctg acc ccc gca gaa ggt gct gac gac ctc aac atc cag cga gtc      248
Arg Leu Thr Pro Ala Glu Gly Ala Asp Asp Leu Asn Ile Gln Arg Val
 55                  60                  65                  70 ctg cgg gtc aac agg acg ctg ttc att ggg gac agg gac aac ctc tac      296
Leu Arg Val Asn Arg Thr Leu Phe Ile Gly Asp Arg Asp Asn Leu Tyr
             75                  80                  85 cgc gta gag ctg gag ccc ccc acg tcc acg gag ctg cgg tac cag agg      344
Arg Val Glu Leu Glu Pro Pro Thr Ser Thr Glu Leu Arg Tyr Gln Arg
         90                  95                 100 aag ctg acc tgg aga tct aac ccc agc gac ata aac gtg tgt cgg atg      392
Lys Leu Thr Trp Arg Ser Asn Pro Ser Asp Ile Asn Val Cys Arg Met
            105                 110                 115 aag ggc aaa cag gag ggc gag tgt cga aac ttc gta aag gtg ctg ctc      440
Lys Gly Lys Gln Glu Gly Glu Cys Arg Asn Phe Val Lys Val Leu Leu
        120                 125                 130 ctt cgg gac gag tcc acg ctc ttt gtg tgc ggt tcc aac gcc ttc aac      488
Leu Arg Asp Glu Ser Thr Leu Phe Val Cys Gly Ser Asn Ala Phe Asn
135                 140                 145                 150 ccg gtg tgc gcc aac tac agc ata gac acc ctg cag ccc gtc gga gac      536
Pro Val Cys Ala Asn Tyr Ser Ile Asp Thr Leu Gln Pro Val Gly Asp
                155                 160                 165 aac atc agc ggt atg gcc cgc tgc ccg tac gac ccc aag cac gcc aat      584
Asn Ile Ser Gly Met Ala Arg Cys Pro Tyr Asp Pro Lys His Ala Asn
            170                 175                 180 gtt gcc ctc ttc tct gac ggg atg ctc ttc aca gct act gtt acc gac      632
Val Ala Leu Phe Ser Asp Gly Met Leu Phe Thr Ala Thr Val Thr Asp
        185                 190                 195 ttc cta gcc att gat gct gtc atc tac cgc agc ctc ggg gac agg ccc      680
Phe Leu Ala Ile Asp Ala Val Ile Tyr Arg Ser Leu Gly Asp Arg Pro
200                 205                 210 acc ctg cgc acc gtg aaa cat gac tcc aag tgg ttc aaa gag cct tac      728
Thr Leu Arg Thr Val Lys His Asp Ser Lys Trp Phe Lys Glu Pro Tyr
215                 220                 225                 230 ttt gtc cat gcg gtg gag tgg ggc agc cat gtc tac ttc ttc ttc cgg      776
Phe Val His Ala Val Glu Trp Gly Ser His Val Tyr Phe Phe Phe Arg
                235                 240                 245 gag att gcg atg gag ttt aac tac ctg gag aag gtg gtg gtg tcc cgc      824
Glu Ile Ala Met Glu Phe Asn Tyr Leu Glu Lys Val Val Val Ser Arg
            250                 255                 260 gtg gcc cga gtg tgc aag aac gac gtg gga ggc tcc ccc cgc gtg ctg      872
Val Ala Arg Val Cys Lys Asn Asp Val Gly Gly Ser Pro Arg Val Leu
        265                 270                 275 gag aag cag tgg acg tcc ttc ctg aag gcg cgg ctc aac tgc tct gta      920
Glu Lys Gln Trp Thr Ser Phe Leu Lys Ala Arg Leu Asn Cys Ser Val
280                 285                 290 ccc gga gac tcc cat ttc tac ttc aac gtg ctg cag gct gtc acg ggc      968
Pro Gly Asp Ser His Phe Tyr Phe Asn Val Leu Gln Ala Val Thr Gly
295                 300                 305                 310 gtg gtc agc ctc ggg ggc cgg ccc gtg gtc ctg gcc gtt ttt tcc acg     1016
Val Val Ser Leu Gly Gly Arg Pro Val Val Leu Ala Val Phe Ser Thr
                315                 320                 325 ccc agc aac agc atc cct ggc tcg gct gtc tgc gcc ttt gac ctg aca     1064
Pro Ser Asn Ser Ile Pro Gly Ser Ala Val Cys Ala Phe Asp Leu Thr
            330                 335                 340 cag gtg gca gct gtg ttt gaa ggc cgc ttc cga gag cag aag tcc ccc     1112
Gln Val Ala Ala Val Phe Glu Gly Arg Phe Arg Glu Gln Lys Ser Pro
        345                 350                 355 gag tcc atc tgg acg ccg gtg ccg gag gat cag gtg cct cga ccc cgg     1160
Glu Ser Ile Trp Thr Pro Val Pro Glu Asp Gln Val Pro Arg Pro Arg
            360                 365                 370
```

```
ccc ggg tgc tgc gca gcc ccc ggg atg cag tac aat gcc tcc agc gcc   1208
Pro Gly Cys Cys Ala Ala Pro Gly Met Gln Tyr Asn Ala Ser Ser Ala
375                 380                 385                 390 ttg ccg gat gac atc ctc aac ttt gtc aag acc cac cct ctg atg gac   1256
Leu Pro Asp Asp Ile Leu Asn Phe Val Lys Thr His Pro Leu Met Asp
                395                 400                 405 gag gcg gtg ccc tcg ctg ggc cat gcg ccc tgg atc ctg cgg acc ctg   1304
Glu Ala Val Pro Ser Leu Gly His Ala Pro Trp Ile Leu Arg Thr Leu
            410                 415                 420 atg agg cac cag ctg act cga gtg gct gtg gac gtg gga gcc ggc ccc   1352
Met Arg His Gln Leu Thr Arg Val Ala Val Asp Val Gly Ala Gly Pro
        425                 430                 435 tgg ggc aac cag acc gtt gtc ttc ctg ggt tct gag gcg ggg acg gtc   1400
Trp Gly Asn Gln Thr Val Val Phe Leu Gly Ser Glu Ala Gly Thr Val
440                 445                 450 ctc aag ttc ctc gtc cgg ccc aat gcc agc acc tca ggg acg tct ggg   1448
Leu Lys Phe Leu Val Arg Pro Asn Ala Ser Thr Ser Gly Thr Ser Gly
455                 460                 465                 470 ctc agt gtc ttc ctg gag gag ttt gag acc tac cgg ccg gac agg tgt   1496
Leu Ser Val Phe Leu Glu Glu Phe Glu Thr Tyr Arg Pro Asp Arg Cys
                475                 480                 485 gga cgg ccc ggc ggt ggc gag aca ggg cag cgg ctg ctg agc ttg gag   1544
Gly Arg Pro Gly Gly Gly Glu Thr Gly Gln Arg Leu Leu Ser Leu Glu
            490                 495                 500 ctg gac gca gct tcg ggg ggc ctg ctg gct gcc ttc ccc cgc tgc gtg   1592
Leu Asp Ala Ala Ser Gly Gly Leu Leu Ala Ala Phe Pro Arg Cys Val
        505                 510                 515 gtc cga gtg cct gtg gct cgc tgc cag cag tac tcg ggg tgt atg aag   1640
Val Arg Val Pro Val Ala Arg Cys Gln Gln Tyr Ser Gly Cys Met Lys
520                 525                 530 aac tgt atc ggc agt cag gac ccc tac tgc ggg tgg gcc ccc gac ggc   1688
Asn Cys Ile Gly Ser Gln Asp Pro Tyr Cys Gly Trp Ala Pro Asp Gly
535                 540                 545                 550 tcc tgc atc ttc ctc agc ccg ggc acc aga gcc gcc ttt gag cag gac   1736
Ser Cys Ile Phe Leu Ser Pro Gly Thr Arg Ala Ala Phe Glu Gln Asp
                555                 560                 565 gtg tcc ggg gcc agc acc tca ggc tta ggg gac tgc aca gga ctc ctg   1784
Val Ser Gly Ala Ser Thr Ser Gly Leu Gly Asp Cys Thr Gly Leu Leu
            570                 575                 580 cgg gcc agc ctc tcc gag gac cgc gcg ggg ctg gtg tcg gtg aac ctg   1832
Arg Ala Ser Leu Ser Glu Asp Arg Ala Gly Leu Val Ser Val Asn Leu
        585                 590                 595 ctg gta acg tcg tcg gtg gcg gcc ttc gtg gtg gga gcc gtg gtg tcc   1880
Leu Val Thr Ser Ser Val Ala Ala Phe Val Val Gly Ala Val Val Ser
600                 605                 610 ggc ttc agc gtg ggc tgg ttc gtg ggc ctc cgt gag cgg cgg gag ctg   1928
Gly Phe Ser Val Gly Trp Phe Val Gly Leu Arg Glu Arg Arg Glu Leu
615                 620                 625                 630 gcc cgg cgc aag gac aag gag gcc atc ctg gcg cac ggg gcg ggc gag   1976
Ala Arg Arg Lys Asp Lys Glu Ala Ile Leu Ala His Gly Ala Gly Glu
                635                 640                 645 gcg gtg ctg agc gtc agc cgc ctg ggc gag cgc agg gcg cag ggt ccc   2024
Ala Val Leu Ser Val Ser Arg Leu Gly Glu Arg Arg Ala Gln Gly Pro
            650                 655                 660 ggg ggc cgg ggc gga ggt ggc ggt ggc gcc ggg gtt ccc ccg gag       2072
Gly Gly Arg Gly Gly Gly Gly Gly Gly Ala Gly Val Pro Pro Glu
        665                 670                 675 gcc ctg ctg gcg ccc ctg atg cag aac ggc tgg gcc aag gcc acg ctg   2120
Ala Leu Leu Ala Pro Leu Met Gln Asn Gly Trp Ala Lys Ala Thr Leu
680                 685                 690
```

-continued

| | |
|---|---|
| ctg cag ggc ggg ccc cac gac ctg gac tcg ggg ctg ctg ccc acg ccc<br>Leu Gln Gly Gly Pro His Asp Leu Asp Ser Gly Leu Leu Pro Thr Pro<br>695                      700                        705                  710 | 2168 |
| gag cag acg ccg ctg ccg cag aag cgc ctg ccc act ccg cac ccg cac<br>Glu Gln Thr Pro Leu Pro Gln Lys Arg Leu Pro Thr Pro His Pro His<br>                715                        720                        725 | 2216 |
| ccc cac gcc ctg ggc ccc cgc gcc tgg gac cac ggc cac ccc ctg ctc<br>Pro His Ala Leu Gly Pro Arg Ala Trp Asp His Gly His Pro Leu Leu<br>            730                        735                        740 | 2264 |
| ccg gcc tcc gct tca tcc tcc ctg ctg ctg gcg ccc gcc cgg gcc<br>Pro Ala Ser Ala Ser Ser Ser Leu Leu Leu Leu Ala Pro Ala Arg Ala<br>745                      750                        755 | 2312 |
| ccc gag cag ccc ccc gcg cct ggg gag ccg acc ccc gac ggc cgc ctc<br>Pro Glu Gln Pro Pro Ala Pro Gly Glu Pro Thr Pro Asp Gly Arg Leu<br>            760                        765                        770 | 2360 |
| tat gct gcc cgg ccc ggc cgc gcc tcc cac ggc gac ttc ccg ctc acc<br>Tyr Ala Ala Arg Pro Gly Arg Ala Ser His Gly Asp Phe Pro Leu Thr<br>775                      780                        785                  790 | 2408 |
| ccc cac gcc agc ccg gac cgc cgg cgg gtg gtg tcc gcg ccc acg ggc<br>Pro His Ala Ser Pro Asp Arg Arg Arg Val Val Ser Ala Pro Thr Gly<br>                795                        800                        805 | 2456 |
| ccc ttg gac cca gcc tca gcc gcc gat ggc ctc ccg cgg ccc tgg agc<br>Pro Leu Asp Pro Ala Ser Ala Ala Asp Gly Leu Pro Arg Pro Trp Ser<br>            810                        815                        820 | 2504 |
| ccg ccc ccg acg ggc agc ctg agg agg cca ctg ggc ccc cac gcc cct<br>Pro Pro Pro Thr Gly Ser Leu Arg Arg Pro Leu Gly Pro His Ala Pro<br>825                      830                        835 | 2552 |
| ccg gcc gcc acc ctg cgc cgc acc cac acg ttc aac agc ggc gag gcc<br>Pro Ala Ala Thr Leu Arg Arg Thr His Thr Phe Asn Ser Gly Glu Ala<br>            840                        845                        850 | 2600 |
| cgg cct ggg gac cgc cac cgc ggc tgc cac gcc cgg ccg ggc aca gac<br>Arg Pro Gly Asp Arg His Arg Gly Cys His Ala Arg Pro Gly Thr Asp<br>855                      860                        865                  870 | 2648 |
| ttg gcc cac ctc ctc ccc tat ggg ggg gcg gac agg act gcg ccc ccc<br>Leu Ala His Leu Leu Pro Tyr Gly Gly Ala Asp Arg Thr Ala Pro Pro<br>                875                        880                        885 | 2696 |
| gtg ccc taggccgggg gccccccgat gccttggcag tgccagccac gggaaccagg<br>Val Pro | 2752 |
| agcgagagac ggtgccagaa cgccggggcc cggggcaact ccgagtgggt gctcaagtcc | 2812 |
| cccccgcgac ccacccgcgg agtgggggc cccctccgcc acaaggaagc acaaccagct | 2872 |
| cgccctcccc ctaccggggg ccgcaggacg ctgagacggt ttgggggtgg gtgggcggga | 2932 |
| ggactttgct atggatttga ggttgacctt atgcgcgtag gttttggttt ttttttgcagt | 2992 |
| tttggtttct tttgcggttt tctaaccaat tgcacaactc cgttctcggg gtggcggcag | 3052 |
| gcaggggagg cttggacgcc ggtgggggaat ggggggccac agctgcagac ctaagccctc | 3112 |
| ccccaccct ggaaaggtcc ctccccaacc caggcccctg gcgtgtgtgg gtgtgcgtgc | 3172 |
| gtgtgcgtgc cgtgttcgtg tgcaagggc cggggaggtg ggcgtgtgtg tgcgtgccag | 3232 |
| cgaaggctgc tgtgggcgtg tgtgtcaagt gggccacgcg tgcagggtgt gtgtccacga | 3292 |
| gcgacgatcg tggtggcccc agcggcctgg gcgttggctg agccgacgct gggcttcca | 3352 |
| gaaggcccgg gggtctccga ggtgccggtt aggagtttga acccccccca ctctgcagag | 3412 |
| ggaagcgggg acaatgccgg ggtttcaggc aggagacacg aggagggcct gcccggaagt | 3472 |
| cacatcggca gcagctgtct aaagggcttg ggggcctggg gggcggcgaa ag | 3524 |

-continued

```
<210> SEQ ID NO 4
<211> LENGTH: 888
<212> TYPE: PRT
<213> ORGANISM: Homo sapiens

<400> SEQUENCE: 4

Met Gln Thr Pro Arg Ala Ser Pro Pro Arg Pro Ala Leu Leu Leu Leu
1               5                   10                  15

Leu Leu Leu Leu Gly Gly Ala His Gly Leu Phe Pro Glu Asp Pro Pro
            20                  25                  30

Pro Leu Ser Val Ala Pro Arg Asp Tyr Leu Asn His Tyr Pro Val Phe
        35                  40                  45

Val Gly Ser Gly Pro Gly Arg Leu Thr Pro Ala Glu Gly Ala Asp Asp
50                  55                  60

Leu Asn Ile Gln Arg Val Leu Arg Val Asn Arg Thr Leu Phe Ile Gly
65                  70                  75                  80

Asp Arg Asp Asn Leu Tyr Arg Val Glu Leu Pro Pro Thr Ser Thr
                85                  90                  95

Glu Leu Arg Tyr Gln Arg Lys Leu Thr Trp Arg Ser Asn Pro Ser Asp
            100                 105                 110

Ile Asn Val Cys Arg Met Lys Gly Lys Gln Glu Gly Glu Cys Arg Asn
        115                 120                 125

Phe Val Lys Val Leu Leu Leu Arg Asp Glu Ser Thr Leu Phe Val Cys
130                 135                 140

Gly Ser Asn Ala Phe Asn Pro Val Cys Ala Asn Tyr Ser Ile Asp Thr
145                 150                 155                 160

Leu Gln Pro Val Gly Asp Asn Ile Ser Gly Met Ala Arg Cys Pro Tyr
                165                 170                 175

Asp Pro Lys His Ala Asn Val Ala Leu Phe Ser Asp Gly Met Leu Phe
            180                 185                 190

Thr Ala Thr Val Thr Asp Phe Leu Ala Ile Asp Ala Val Ile Tyr Arg
        195                 200                 205

Ser Leu Gly Asp Arg Pro Thr Leu Arg Thr Val Lys His Asp Ser Lys
210                 215                 220

Trp Phe Lys Glu Pro Tyr Phe Val His Ala Val Glu Trp Gly Ser His
225                 230                 235                 240

Val Tyr Phe Phe Phe Arg Glu Ile Ala Met Glu Phe Asn Tyr Leu Glu
                245                 250                 255

Lys Val Val Val Ser Arg Val Ala Arg Val Cys Lys Asn Asp Val Gly
            260                 265                 270

Gly Ser Pro Arg Val Leu Glu Lys Gln Trp Thr Ser Phe Leu Lys Ala
        275                 280                 285

Arg Leu Asn Cys Ser Val Pro Gly Asp Ser His Phe Tyr Phe Asn Val
290                 295                 300

Leu Gln Ala Val Thr Gly Val Val Ser Leu Gly Gly Arg Pro Val Val
305                 310                 315                 320

Leu Ala Val Phe Ser Thr Pro Ser Asn Ser Ile Pro Gly Ser Ala Val
                325                 330                 335

Cys Ala Phe Asp Leu Thr Gln Val Ala Ala Val Phe Glu Gly Arg Phe
            340                 345                 350

Arg Glu Gln Lys Ser Pro Glu Ser Ile Trp Thr Pro Val Pro Glu Asp
        355                 360                 365

Gln Val Pro Arg Pro Arg Pro Gly Cys Cys Ala Ala Pro Gly Met Gln
370                 375                 380
```

```
-continued

Tyr Asn Ala Ser Ser Ala Leu Pro Asp Asp Ile Leu Asn Phe Val Lys
385                 390                 395                 400

Thr His Pro Leu Met Asp Glu Ala Val Pro Ser Leu Gly His Ala Pro
            405                 410                 415

Trp Ile Leu Arg Thr Leu Met Arg His Gln Leu Thr Arg Val Ala Val
                420                 425                 430

Asp Val Gly Ala Gly Pro Trp Gly Asn Gln Thr Val Val Phe Leu Gly
            435                 440                 445

Ser Glu Ala Gly Thr Val Leu Lys Phe Leu Val Arg Pro Asn Ala Ser
450                 455                 460

Thr Ser Gly Thr Ser Gly Leu Ser Val Phe Leu Glu Glu Phe Glu Thr
465                 470                 475                 480

Tyr Arg Pro Asp Arg Cys Gly Arg Pro Gly Gly Glu Thr Gly Gln
                485                 490                 495

Arg Leu Leu Ser Leu Glu Leu Asp Ala Ala Ser Gly Gly Leu Leu Ala
            500                 505                 510

Ala Phe Pro Arg Cys Val Val Arg Val Pro Val Ala Arg Cys Gln Gln
                515                 520                 525

Tyr Ser Gly Cys Met Lys Asn Cys Ile Gly Ser Gln Asp Pro Tyr Cys
            530                 535                 540

Gly Trp Ala Pro Asp Gly Ser Cys Ile Phe Leu Ser Pro Gly Thr Arg
545                 550                 555                 560

Ala Ala Phe Glu Gln Asp Val Ser Gly Ala Ser Thr Ser Gly Leu Gly
                565                 570                 575

Asp Cys Thr Gly Leu Leu Arg Ala Ser Leu Ser Glu Asp Arg Ala Gly
            580                 585                 590

Leu Val Ser Val Asn Leu Leu Val Thr Ser Ser Val Ala Ala Phe Val
            595                 600                 605

Val Gly Ala Val Ser Gly Phe Ser Val Gly Trp Phe Val Gly Leu
            610                 615                 620

Arg Glu Arg Arg Glu Leu Ala Arg Arg Lys Asp Lys Glu Ala Ile Leu
625                 630                 635                 640

Ala His Gly Ala Gly Glu Ala Val Leu Ser Val Ser Arg Leu Gly Glu
                645                 650                 655

Arg Arg Ala Gln Gly Pro Gly Arg Gly Gly Gly Gly Gly Gly
            660                 665                 670

Ala Gly Val Pro Pro Glu Ala Leu Leu Ala Pro Leu Met Gln Asn Gly
            675                 680                 685

Trp Ala Lys Ala Thr Leu Leu Gln Gly Gly Pro His Asp Leu Asp Ser
690                 695                 700

Gly Leu Leu Pro Thr Pro Glu Gln Thr Pro Leu Pro Gln Lys Arg Leu
705                 710                 715                 720

Pro Thr Pro His Pro His Pro His Ala Leu Gly Pro Arg Ala Trp Asp
            725                 730                 735

His Gly His Pro Leu Leu Pro Ala Ser Ala Ser Ser Leu Leu Leu
            740                 745                 750

Leu Ala Pro Ala Arg Ala Pro Glu Gln Pro Ala Pro Gly Glu Pro
            755                 760                 765

Thr Pro Asp Gly Arg Leu Tyr Ala Ala Arg Pro Gly Arg Ala Ser His
            770                 775                 780

Gly Asp Phe Pro Leu Thr Pro His Ala Ser Pro Asp Arg Arg Val
785                 790                 795                 800
```

```
Val Ser Ala Pro Thr Gly Pro Leu Asp Pro Ala Ser Ala Ala Asp Gly
                805                 810                 815

Leu Pro Arg Pro Trp Ser Pro Pro Thr Gly Ser Leu Arg Arg Pro
            820                 825                 830

Leu Gly Pro His Ala Pro Pro Ala Ala Thr Leu Arg Arg Thr His Thr
            835                 840                 845

Phe Asn Ser Gly Glu Ala Arg Pro Gly Asp Arg His Arg Gly Cys His
        850                 855                 860

Ala Arg Pro Gly Thr Asp Leu Ala His Leu Leu Pro Tyr Gly Ala
865                 870                 875                 880

Asp Arg Thr Ala Pro Pro Val Pro
                885

<210> SEQ ID NO 5
<211> LENGTH: 8
<212> TYPE: PRT
<213> ORGANISM: Artificial Sequence
<220> FEATURE:
<223> OTHER INFORMATION: Derived from Homo sapiens

<400> SEQUENCE: 5

Gln Asp Pro Tyr Cys Gly Trp Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Consensus sequences found in Semaphorins of
      various species
<221> NAME/KEY: misc_feature
<222> LOCATION: (1)..(1)
<223> OTHER INFORMATION: Xaa is Gln or Arg
<221> NAME/KEY: misc_feature
<222> LOCATION: (4)..(4)
<223> OTHER INFORMATION: Xaa is Tyr or His
<221> NAME/KEY: misc_feature
<222> LOCATION: (6)..(6)
<223> OTHER INFORMATION: Xaa is Ala or Gly

<400> SEQUENCE: 6

Xaa Asp Pro Xaa Cys Xaa Trp Asp
1               5

<210> SEQ ID NO 7
<211> LENGTH: 176
<212> TYPE: DNA
<213> ORGANISM: Artificial Sequence
<220> FEATURE:
<223> OTHER INFORMATION: Derived from Homo sapiens

<400> SEQUENCE: 7
cagcggctgc tgagcttgga gctggacgca gcttcggggg gcctgctggc tgccttcccc      60
cgctgcgtgg tccgagtgcc tgtggctcgc tgccagcagt actcggggtg tatgaagaac     120
tgtatcggca gtcaggaccc ctactgcggg tgggcccccg acggctcctg catctt         176

<210> SEQ ID NO 8
<211> LENGTH: 18
<212> TYPE: DNA
<213> ORGANISM: Artificial Sequence
<220> FEATURE:
<223> OTHER INFORMATION: Derived from Homo sapiens
```

```
<400> SEQUENCE: 8
aagatgcagg agccgtcg                                          18

<210> SEQ ID NO 9
<211> LENGTH: 18
<212> TYPE: DNA
<213> ORGANISM: Artificial Sequence
<220> FEATURE:
<223> OTHER INFORMATION: Primer targeted to Homo sapiens

<400> SEQUENCE: 9
cagcggctgc tgagcttg                                          18

<210> SEQ ID NO 10
<211> LENGTH: 21
<212> TYPE: DNA
<213> ORGANISM: Artificial Sequence
<220> FEATURE:
<223> OTHER INFORMATION: Primer derived from Rattus norvegicus

<400> SEQUENCE: 10
tacttcaatg tactgcaggc t                                      21

<210> SEQ ID NO 11
<211> LENGTH: 21
<212> TYPE: DNA
<213> ORGANISM: Artificial Sequence
<220> FEATURE:
<223> OTHER INFORMATION: Primer derived from Rattus norvegicus

<400> SEQUENCE: 11
aagatgcagg agccatcggg g                                      21

<210> SEQ ID NO 12
<211> LENGTH: 18
<212> TYPE: DNA
<213> ORGANISM: Artificial Sequence
<220> FEATURE:
<223> OTHER INFORMATION: Primer targeted to Rattus norvegicus

<400> SEQUENCE: 12
caggaacacg aaccacac                                          18

<210> SEQ ID NO 13
<211> LENGTH: 18
<212> TYPE: DNA
<213> ORGANISM: Artificial Sequence
<220> FEATURE:
<223> OTHER INFORMATION: Primer targeted to Rattus norvegicus

<400> SEQUENCE: 13
gtatgcaaga atgatgtg                                          18

<210> SEQ ID NO 14
<211> LENGTH: 20
<212> TYPE: DNA
<213> ORGANISM: Artificial Sequence
<220> FEATURE:
<223> OTHER INFORMATION: Adapter DNA used to ligate the various parts of
      the pRSZinc plasmid

<400> SEQUENCE: 14
tcgagatctg cagctgacgt                                        20
```

<210> SEQ ID NO 15
<211> LENGTH: 12
<212> TYPE: DNA
<213> ORGANISM: Artificial Sequence
<220> FEATURE:
<223> OTHER INFORMATION: Adapter DNA used to ligate the various parts of
      the pRSZinc plasmid

<400> SEQUENCE: 15
cagctgcaga tc                                                          12

<210> SEQ ID NO 16
<211> LENGTH: 32
<212> TYPE: DNA
<213> ORGANISM: Artificial Sequence
<220> FEATURE:
<223> OTHER INFORMATION: Adapter DNA used to ligate the various parts of
      the rSZexII plasmid

<400> SEQUENCE: 16
tcgagctgtg actggtgtgg tgacggttcc cg                                    32

<210> SEQ ID NO 17
<211> LENGTH: 31
<212> TYPE: DNA
<213> ORGANISM: Artificial Sequence
<220> FEATURE:
<223> OTHER INFORMATION: Adapter DNA used to ligate the various parts of
      the rSZexII plasmid

<400> SEQUENCE: 17
ggccgccaag gctcaccaca ccagtcacag c                                     31

<210> SEQ ID NO 18
<211> LENGTH: 13
<212> TYPE: DNA
<213> ORGANISM: Artificial Sequence
<220> FEATURE:
<223> OTHER INFORMATION: Adapter DNA used to ligate the various parts of
      the rSZexII plasmid

<400> SEQUENCE: 18
cctgataata gtt                                                         13

<210> SEQ ID NO 19
<211> LENGTH: 19
<212> TYPE: DNA
<213> ORGANISM: Artificial Sequence
<220> FEATURE:
<223> OTHER INFORMATION: Adapter DNA used to ligate the various parts of
      the rSZexII plasmid

<400> SEQUENCE: 19
cgaactatta tcaggacgt                                                   19

<210> SEQ ID NO 20
<211> LENGTH: 176
<212> TYPE: DNA
<213> ORGANISM: Homo sapiens
<220> FEATURE:
<221> NAME/KEY: misc_feature
<222> LOCATION: (1)..(176)
<223> OTHER INFORMATION: n is any nucleotide base (A, T, G, or C)

-continued

```
<400> SEQUENCE: 20
aagatgcagg agccgtcggg ggcccacccg cagtaggggt cctgactgcc gatacagntc      60
ttcatacacc nngagtactg ctggcagcga gccacaggca ctcggaccac gcagcgggng     120
anggcagcca gcaggccccc cgaagctgcg tccanctcca agctcagcag ccgctg         176
```

SEMAPHORIN Z AND GENE ENCODING THE SAME

Figure 1:
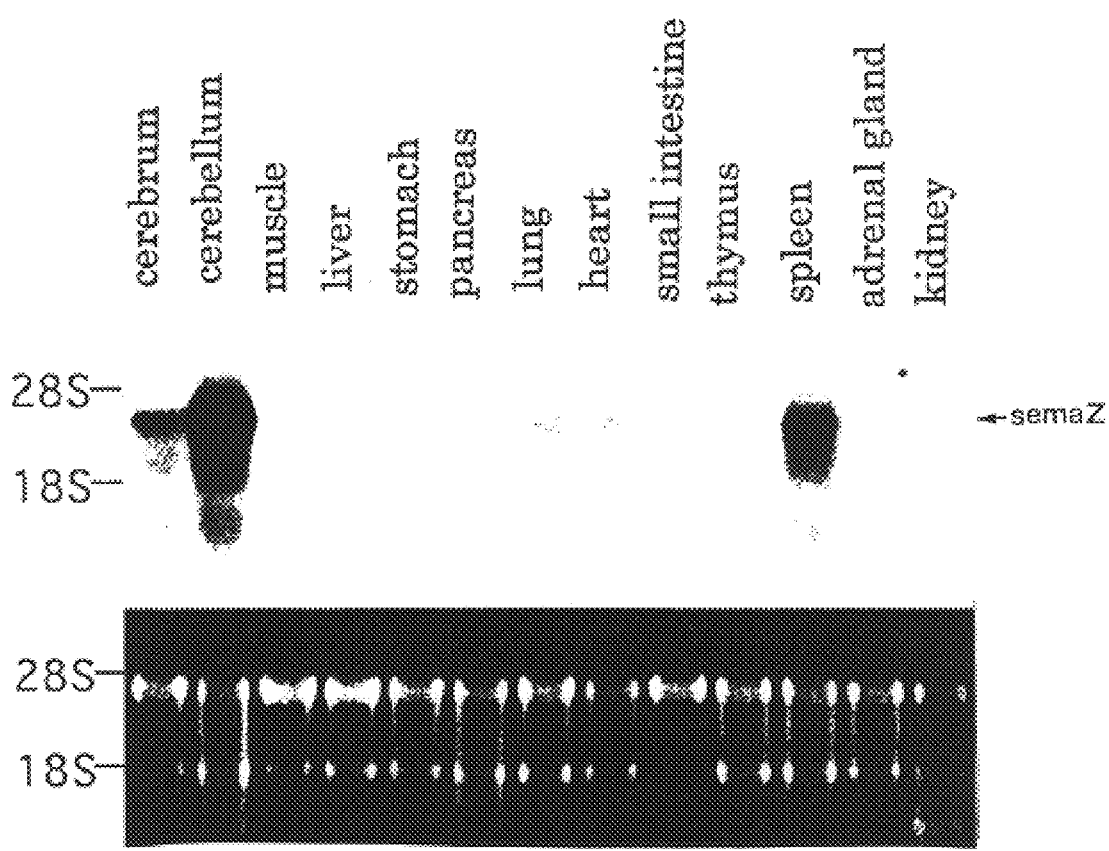

This application claims the benefit under 35 U.S.C. §371 of prior PCT International Application No. PCT/JP96/03517 which has an International filing date of Dec. 2, 1996 which designated the United States of America, the entire contents of which are hereby incorporated by references.

TECHNICAL FIELD

The present invention relates to Semaphorin Z, a novel Semaphorin belonging to the Semaphorin family, and use of Semaphorin Z for pharmaceutical agents or laboratory reagents. More particularly, it relates to Semaphorin Z inhibiting neurite outgrowth, and a gene encoding the same, as well as other Semaphorins hybridizing to said Semaphorin Z gene. Furthermore, the present invention relates to modified proteins or partial peptides of Semaphorin Z, antibodies against Semaphorin Z, DNAs or RNAs complementary to said Semaphorin Z gene, and their use for pharmaceutical or diagnostic agents or laboratory reagents.

BACKGROUND ART

It is widely known that a central nervous system (CNS)-neuron in higher organisms such as human is not capable of regeneration once injured. Therefore, one who has received an injury on his (her) spinal cord due to, for example, a traffic accident is compelled to spend the rest of his (her) life in a hemiplegic state. On the contrary, it is known that a peripheral nervous system (PNS)-neuron retains a vigorous regeneration ability even in those higher organisms, and therefore, neurons in a limb, when disconnected, can gradually regenerate with a concomitant recovery of their function.

In early nineteen-eighties, a group of Aguayo et al. found that when PNS-neuron is experimentally grafted into an injured CNS-neuron in a higher organism, axon growth of CNS-neuron is induced. This observation demonstrates that CNS-neuron in higher organisms which had been generally considered not to have a regeneration ability can regenerate if a suitable environment is provided (*Nature*, 284, 264–265 (1980), *Science*, 214, 931–933 (1981)). That report suggests a possibility that in CNS of higher organisms, there may exist a factor, namable "CNS-neuron regeneration inhibitor", which inhibits the regeneration of CNS-neuron, and that a release from such inhibition may allow the regeneration of CNS-neurons. This suggestion paved the way for a CNS-neuron regeneration therapy.

In 1988, a group of Schwab et al. demonstrated that there existed such CNS-neuron regeneration inhibitor among proteins derived from CNS myelin. They also succeeded in purifying, though partially, a protein having said CNS-neuron regeneration inhibition activity, and named this protein fraction NI35/250 (*Annu. Rev. Neurosci.*, 16, 565–595 (1993)), although no one has succeeded in its isolation, identification and gene cloning yet. In addition, they immunized animals with the partial purified NI35/250, and succeeded in obtaining an antibody (IN-1) having a neutralizing activity. This antibody is capable of recognizing a band for NI35/250 in Western blotting, and capable of staining, in an immunostaining, the region where NI35/250 is supposed to be distributed. Furthermore, they demonstrated that administration of this antibody to an animal experimentally received an injury on its spinal cord has promoted regeneration of axons in spinal cord, though partially, within 2–3 weeks, and restored its function within 2–3 months (*Nature*, 343, 269–272 (1990), *Nature*, 378, 498–501 (1995)). These findings are of great value, because they experimentally demonstrated that there existed a CNS-neuron regeneration inhibitor as suggested by Aguayo et al. (supra) and that CNS-neuron can be regenerated by inhibiting the activity of said inhibitor. The above noted antibody is, however, directed not to human but to rat NI35/250, and exhibits a low stability and specificity. In addition, although regeneration of CNS-neuron was observed as described above by administering said antibody, its effect was so partial and incomplete that not all of the motor functions could be restored. It is, therefore, believed essential in solving these problems to identify the gene coding for NI35/250 or corresponding CNS-neuron regeneration inhibitor, and, based on knowledges of molecular biology, neuroscience and the like, develop an inhibitor effectively inhibiting the CNS-neuron regeneration inhibition activity, or develop a method for inhibiting the expression of the gene for said regeneration inhibitor.

Apart from the above, the nervous system, whether it is central or peripheral, requires formation of a complicated neural network among neurons or between neurons and peripheral receivers or effectors during development, that is, in the stage of embryo or fetus, in order to precisely carry out its principal functions, i.e., to transfer and process the information. To establish the neural network, an ingenious mechanism is necessary, which precisely guides a growing neurite to the target site locating remote therefrom.

It has been hitherto believed that a factor which positively control the neurite outgrowth such as neurite growth promoter and neurite growth attractant may play a major role in the formation of the neural network. However, it is now being demonstrated by recent studies on the mechanism of the network formation that the opposite factor, that is, a negative factor having an outgrowth inhibition activity is important for an accurate guidance (*Cell*, 78, 353–356 (1994)).

A representative factor having such an outgrowth inhibition activity is a protein called "Semaphorin". Semaphorin firstly discovered is Fasciclin IV found in grasshopper. Collapsin (latterly named Collapsin I) was subsequently discovered in chick (*Cell*, 75, 217–227 (1993); *Neuron*, 9, 831–845 (1992)). To date, more than 10 genes belonging to the Semaphorin family have been reported in a wide range of species covering insects such as drosophila and beetle, human, and viruses (*Cell*, 81, 471–474 (1995)). These Semaphorins characteristically contains in their amino acid sequences a certain structure called semaphorin domain consisting of about 500 amino acids (*Neuron*, 14, 941–948 (1995); *Cell*, 75, 1389–1399 (1993)). However, the homologies of the primary amino acid sequences in Semaphorin domains among these Semaphorin genes are 80–20%, and not necessarily high.

Of these Semaphorins, functions have been verified for only a few, including, for example, Fasciclin IV of grasshopper, Semaphorins I and II of drosophila, Collapsin of chick, and Semaphorin III which corresponds to Collapsin in mammals. All of these Semaphorins are known to inhibit neurite outgrowth and synapsis formation. In particular, Semaphorin III has been reported to have an activity collapsing in a short time the growth cone of cultured neuron (growth-cone collapse activity) in vitro (*Neuron*, 14, 941–948 (1995); *Neuron*, 14, 949–959 (1995); *Cell*, 81, 631–639 (1995); *Cell*, 75, 1389–1399 (1993); *Cell*, 75, 217–227 (1993); *Neuron*, 9, 831–845 (1992)).

Although it is now being demonstrated, as described above, that Semaphorin has a growth-cone collapse activity and a neurite outgrowth inhibition activity during development, and plays a role in giving an accurate guidance to neuron, it is not evident at present whether or not Semaphorin exerts some function not only during development but also in the adult, and less evident whether or not Semaphorin plays a role as a CNS-neuron regeneration inhibitor. Of course, since Semaphorin has been shown to be a negative guidance factor inhibiting neurite outgrowth, it would not be unreasonable to consider said Semaphorin as a candidate for a CNS-neuron regeneration inhibitor (*Nature*, 378, 439–440 (1995)). However, it has been shown by in vitro experiments that Semaphorin III (Sema III), only one Semaphorin of higher organisms of which function has been analyzed, exerts its neurite-outgrowth inhibition activity on a sensory neuron and sympathetic neuron both of which are peripheral, but not on a retinal neuron which is central (*Cell*, 75, 217–227 (1993)). In addition, Northern analysis on the distribution of Sema III expression in the adult conducted by the present inventors has revealed that it is expressed mainly in peripheral tissues (see Reference example 2 below). It is therefore hardly believed that Sema III having such features has a function as a "CNS-neuron regeneration inhibitor".

PROBLEM TO BE SOLVED BY THE INVENTION

The present invention aims to provide Semaphorin Z, a novel Semaphorin inhibiting neurite outgrowth, and a gene therefor, and to provide a pharmaceutical or diagnostic agent for neural diseases, in particular an agent for regeneration of CNS-neuron, as well as a laboratory reagent. Based on the discovery of Semaphorin Z, the present invention also provides, for example, another Semaphorin gene hybridizing to said Semaphorin Z gene, a modified Semaphorin Z protein or a partial peptide of Semaphorin Z, an antibody against Semaphorin Z, DNA or RNA complementary to said Semaphorin Z gene, a screening method for Semaphorin Z inhibitor using Semaphorin Z, a Semaphorin Z inhibitor obtained by said screening method, a pharmaceutical composition comprising Semaphorin Z or an inhibitor thereof, a transgenic animal involving Semaphorin Z. Furthermore, the present invention provides a laboratory reagent for this technical field on the basis of the discovery of Semaphorin Z.

MEANS FOR SOLVING THE PROBLEM

If regeneration of CNS-neuron in the adult is always kept inhibited as described in the "Prior Art" section, it is believed that identification of a factor which inhibits regeneration of CNS-neuron is the most important subject to be solved for establishing a therapy for regeneration of CNS-neuron, and that any therapy for regeneration of CNS-neuron can not be established without identifying such factor.

The present inventors have paid their attention to the similarity between the in vitro activities of the above-described NI35/250 and Semaphorin, a negative guidance factor. Specifically, the present inventors have paid their attention to the fact that NI35/250 has a growth-cone collapse activity and a neurite-growth inhibition activity in vitro (*J. Neurosci.*, 8, 2381–2393 (1988); *Science*, 259, 80 (1993)), while known Semaphorins similarly possess a neurite-growth inhibition activity, and particularly Semaphorin III has also a growth-cone collapse activity. This suggested to the inventors the possibility that unknown Semaphorins which have not yet been identified may include the one having a function as a CNS-neuron regeneration inhibitor. Specifically, the present inventors' idea was that, although Semaphorin, which is characterized in that 1) it is highly expressed in CNS of adult and 2) it is poorly expressed in fetus or peripheral tissues in adult where the neurite outgrowth is not inhibited, has not been identified yet, if one can identify a new unknown Semaphorin having such characteristics, the Semaphorin might function as a CNS-neuron regeneration inhibitor.

Thus, a DNA sequence encoding amino acids relatively well conserved among previously reported Semaphorin genes was firstly determined using EST (Expressed Sequence Tags) database, and as a consequence, a DNA fragment T08532(SEQ ID NO:20) was identified, which encodes, as a partial sequence, a sequence (Gln-Asp-Pro-Tyr-Cys-Gly-Trp-Ala) (SEQ ID NO:5)similar to that consisting of 8 amino acids highly conserved among Semaphorins (Gln (or Arg)-Asp-Pro-Tyr (or His)-Cys-Ala (or Gly)-Trp-Asp) (SEQ ID NO:6).

This T08532(SEQ ID NO:20) sequence contained undetermined bases, and its open reading frame could not be determined. Furthermore, T08532(SEQ ID NO:20) almost never contained any sequence which is common to Semaphorins, with the exception of the above amino acid sequence. Therefore, it could not be concluded at that stage that T08532(SEQ ID NO:20) is part of the gene encoding "Semaphorin". Furthermore, distribution of T08532(SEQ ID NO:20) in fetus and adult tissues was absolutely unclear, and it was utterly impossible to expect that T08532(SEQ ID NO:20) may be a part of the gene encoding a Semaphorin having a function as a "CNS-neuron regeneration inhibitor".

Thus, a DNA primer was firstly synthesized on the basis of the sequence information of T08532(SEQ ID NO:20), and used in PCR reaction together with cDNAs prepared from human hippocampal cDNA library as a template to clone a region corresponding to T08532(SEQ ID NO:20) and determine the base sequence (SEQ ID NO:7). Using the fragment thus cloned, rat and human cDNA libraries were then screened. As a result, the rat and human genes cloned in this procedures proved to be a novel Semaphorin gene having a sequence characteristic to Semaphorins. We named this novel Semaphorin "Semaphorin Z".

Subsequent analysis revealed that Semaphorin Z of the present invention is highly expressed in CNS in the adult, but scarcely expressed in other tissues except for spleen, and that its expression in embryos was considerably lower than that in the adult, demonstrating an expression distribution which is considered reasonable for "CNS-neuron regeneration inhibitor".

In addition, the present inventors have found that Semaphorin Z of the present invention has an inhibitory effect on neurite outgrowth. Furthermore, it has been found that a gene having a sequence complementary to Semaphorin Z gene inhibits the expression of Semaphorin Z.

Semaphorin Z of the present invention appears to be a CNS-neuron regeneration inhibitor in the adult, since it is highly expressed in CNS and inhibits neurite outgrowth as described above. The use of Semaphorin Z permits carrying out a screening to obtain Semaphorin Z inhibitor, and the inhibitor found by such screening system will be able to promote regeneration of CNS-neuron. Furthermore, since a gene having a sequence complementary to Semaphorin Z gene has inhibited the expression of Semaphorin Z as described above, such complementary gene may be used in a therapy for regeneration of CNS-neuron.

In addition, in view of the fact that Semaphorin Z of the present invention inhibits neurite outgrowth as described above, it may be used as a therapeutic or diagnostic agent for pains or immune diseases such as atopic dermatitis, by administering to peripheral tissues, which results in the inhibition of neurite outgrowth of PNS-neuron. Furthermore, since Semaphorin Z is a novel Semaphorin belonging to the Semaphorin family, it serves as an important research material or a laboratory reagent.

The present invention has been completed on the basis of the above findings.

That is, the gist of the present invention is as follows:
(1) Semaphorin Z DNA comprising the nucleotide sequence shown in SEQ ID NO: 1 or 3;
(2) Semaphorin Z open reading frame comprising the nucleotide sequence shown in residues 19 through 2682 of SEQ ID NO:1 or residues 39 though2702of SEQ ID NO: 3;
(3) Semaphorin Z protein comprising the amino acid sequence shown in SEQ ID NO: 2 or 4;
(4) DNA which encodes a protein having Semaphorin domain and which hybridizes under stringent conditions to DNA comprising the nucleotide sequence shown in SEQ ID NO: 7;
(5) a protein encoded by the DNA of the above item (4);
(6) DNA which encodes a protein inhibiting neurite outgrowth and which hybridizes under stringent conditions to the DNA of the above item (1);
(7) DNA of the above item (6) which encodes a protein inhibiting neurite outgrowth of CNS-neuron;
(8) a protein encoded by the DNA of the above item (6) or (7);
(9) DNA which encodes a protein inhibiting neurite outgrowth, said protein containing insertions, deletions or substitutions of one or more amino acids in the protein of the above item (3);
(10) DNA of the above item (9) which encodes a protein inhibiting neurite 5 outgrowth of CNS-neuron;
(11) a protein encoded by the DNA of the above item (9) or (10);
(12) DNA which encodes a protein promoting neurite outgrowth of CNS-neuron, said protein containing insertions, deletions, or substitutions of one or more amino acids in the protein of the above item (3);
(13) a protein encoded by the DNA of the above item (12);
(14) DNA which is cloned from a human cDNA or genomic library, and which hybridizes under stringent conditions to DNA comprising at least part of the DNA of the above item (1) or at least part of the complementary strand thereof;
(15) an expression plasmid expressing one of the DNAs of the above items (1), (2), (4), (6), (7), (9), (10), (12), or (14);
(16) a transformant transformed with the expression plasmid of the above item (15);
(17) a process for producing a recombinant protein, said process being characterized in that it comprises culturing the transformant of the above item (16) under conditions in which the expression plasmid of the above item (15) can be expressed;
(18) a polypeptide comprising at least 6 amino acids of one of the proteins of the above items (3), (5), (8), (11), or (13);
(19) a polypeptide of the above item (18) which promotes neurite outgrowth of CNS-neuron;
(20) a polypeptide of the above item (18) characterized in that it contains aspartic acid residue at position 203 of the amino acid sequence shown in SEQ ID NO: 6 or an amino acid residue corresponding to the position of said aspartic acid residue;
(21) DNA or RNA comprising 8 or more bases, or a chemically modified variant thereof, which has a sequence complementary to one of the DNAs of the above items (1), (4), (6), (7), or (14),.;
(22) DNA or RNA of the above item (21), or a chemically modified variant thereof, characterized in that it inhibits an expression of one of the proteins of the above items (3), (5), or (8);
(23) an antibody against one of the proteins of the above items (3), (5), (8), (11), or (13), or against one of the polypeptides of the above items (18)–(20);
(24) a screening method for Semaphorin Z inhibitor, which method is characterized in that it employs one of the proteins of the above items (3), (5), (8), or (11);
(25) Semaphorin Z inhibitor obtained by the screening method of the above item (24);
(26) Semaphorin Z inhibitor of the above item (25) which comprises the protein of the above item (13), the polypeptide of the above item (19) or (20), or the antibody of the above item (23);
(27) a CNS-neuron regeneration promoter which is characterized in that it contains at least one of the DNAs or RNAs of the above item (22) or chemically modified variants thereof, or Semaphorin Z inhibitors of the above item (25) or (26);
(28) a neurite outgrowth inhibitor for PNS-neuron which is characterized in that it contains at least one of the proteins of the above items (3), (5), (8), or (11); and
(29) a transgenic animal in which one of the DNAs of the above items (1), (4), (6), (7), (9), (10), or (12) has been artificially inserted into its chromosome, or has been knocked out.

MODE FOR CARRYING OUT THE INVENTION

The 1st embodiment of the present invention is cDNA for rat Semaphorin Z which comprises the base sequence shown in SEQ ID NO: 1 or cDNA for human Semaphorin Z which comprises the base sequence shown in SEQ ID NO: 3. These DNAs, as described in Example 1, may be cloned by screening a cDNA library derived from CNS tissue using a DNA having the sequence shown in SEQ ID NO: 7 as a probe. Particular techniques for such cloning may be found in a standard text such as "*Molecular Cloning*, 2nd ed.", Cold Spring Harbor Laboratory Press (1989). The nucleotide sequence of the cloned DNA may be determined by conventional methods, for example, using a sequence kit commercially available.

Alternatively, after publication of the nucleotide sequences of rat and human Semaphorin Z cDNAs of the present invention, one skilled in the art can also easily clone the rat and human Semaphorin Z gene in full length using part of said cDNA as a probe or primer, without using the cloning method as described above.

The 2nd embodiment of the present invention is an open reading frame of rat Semaphorin Z gene which comprises the nucleotide sequence shown in residues 19 through 2682 of SEQ ID NO:1 or an open reading frame of human Semaphorin Z gene which comprises the base sequence shown in residues 39 through 2702 of SEQ ID NO:3.

The 3rd embodiment of the present invention is a rat Semaphorin Z protein (referred to hereinafter simply as rat Semaphorin Z) which comprises the amino acid sequence shown in SEQ ID NO: 2 or a human Semaphorin Z protein (referred to hereinafter simply as human Semaphorin Z) which comprises the amino acid sequence shown in SEQ ID NO: 4.

Semaphorin Z contains Semaphorin domain characteristic to Semaphorins and this domain corresponds to a region extending from position 49 to position 580 of the amino acid sequence shown in SEQ ID NO: 2 or a region extending from position 48 to position 578 of the amino acid shown in SEQ ID NO: 4.

Semaphorin Z also contains a signal sequence at its N-terminal and this sequence is presumed to correspond to a region from position 1 to position 26 of the amino acid sequence shown in SEQ ID NO: 2 or from position 1 to position 25 of the amino acid sequence shown in SEQ ID NO: 4. The signal sequence is removed by processing during its transfer to membrane.

Preparation of Semaphorin Z may be achieved, for example, by linking a cloned Semaphorin Z cDNA to a known expression vector such as pET or pCDM8, and introducing the vector into an appropriate host cell to express and produce Semaphorin Z. The host cell may be procaryotic or eukaryotic. For example, *Escherichia coli* strains or animal cell lines are already conventionally used for such purpose and they are commercially available. Examples of animal host cells include COS-1, COS-7, CHO cells and the like.

To transform an appropriate animal host cell with an expression plasmid, a known procedure such as the DEAE-dextran method (*Current Protocols in Molecular Biology*, F. M. Ausubel et al.ed., John Wiley & Sons (1987)) may be used. As demonstrated in Example 7, Semaphorin Z of the present invention is localized in the cell membrane fraction which contains a sufficient amount of Semaphorin Z to be directly used in various assays. Therefore, various assays for Semaphorin Z activity may easily be conducted using the cell membrane fraction.

The cell membrane fraction may easily be prepared by homogenizing Semaphorin Z-expressing cells, isolating and purifying the fraction by centrifugation as described hereinafter in Example 7.

Semaphorin Z may be purified by, for example, an affinity purification using an antibody against Semaphorin Z described hereinafter in the section of the 23rd embodiment of the present invention, or conventional column chromatography.

The 4th embodiment of the present invention is a DNA which encodes a protein having semaphorin domain and which hybridizes under stringent conditions to DNA comprising the nucleotide sequence shown in SEQ ID NO: 7.

In the above description, "DNA comprising the nucleotide sequence shown in SEQ ID NO: 7" refers to a fragment cloned from cDNA by PCR reaction using the sequence information of the DNA "T08532" which encodes, in a part, a sequence (Gln-Asp-Pro-Tyr-Cys-Gly-Trp-Ala SEQ ID NO: 5) similar to the eight amino-acid sequence well conserved among Semaphorins (Gln (or Arg)-Asp-Pro-Tyr (or His)-Cys-Ala (or Gly)-Trp-Asp SEQ ID NO: 6). The DNA fragment corresponds to a region from position 1510 to position 1685 in the nucleotide sequence of rat Semaphorin Z shown in SEQ ID NO: 1, or a region from position 1524 to position 1699 in the nucleotide sequence of human Semaphorin Z shown in SEQ ID NO: 3.

As used herein, DNA which "hybridizes under stringent conditions" refers to such a DNA that hybridizes to DNA of SEQ ID NO: 7, for example, when hybridized under the following conditions: a formamide concentration of about 45% (v/v), a salt concentration of about 5×SSPE, and a temperature of about 42° C., and washed under the following conditions: a salt concentration of 2×SSPE, and a temperature of about 42° C., as described in Example 1.

Cloning of these DNAs is achieved by, for example, hybridization with DNA of SEQ ID NO: 7, and specifically may be carried out, for example, according to the procedures described in *TINS*, 15, 319–323 (1992) and references cited therein, and more specifically according to the following procedures.

That is, the cloning may be achieved by screening a cDNA or genomic library prepared from one of various animal tissues using DNA consisting of the nucleotide sequence shown in SEQ ID NO: 7 as a probe. The screening may be carried out according to, for example, the procedures as described in Example 1. Preferred cDNA libraries are those derived from an adult tissue of CNS, and a cDNA library derived from hippocampus, corpus striatum, or cerebellum is more preferred. As described above, the conditions shown in Example 1 or those described in *TINS*, 15, 319–323 (1992) and references cited therein may be used for the hybridization.

The DNA of the 4th embodiment of the present invention is also "DNA which encodes a protein having semaphorin domain". As used herein, "semaphorin domain" refers to a domain consisting of 300–600 amino acid residues more than 20% of which are identical to those amino acid residues constituting semaphorin domain of one of 10 known Semaphorins (G-Sema I, T-Sema, I, D-Sema II, H-Sema III, C-Collapsin, Sem A, Sem B, Sem C, Sem D, Sem E) described in, for example, *Cell*, 75, 1389–1399 (1993) or *Neuron*, 14, 941–948 (1995). Those proteins having semaphorin domain more than 30% of which amino acids are identical to those amino acids of one of the known Semaphorins are particularly preferred. The identity of amino acids is determined by comparison using, for example, DNASIS Ver. 2.0 (HITACH Software Engineering) under conditions of ktup=1 and cutoff=1. More preferred proteins are those in which 10 or more cysteines, particularly 12 or more cysteines, of the 13 cysteines conserved in Semaphorin domains of the 10 known Semaphorins (for example, those cysteines marked in FIG. 1 on page 942 of *Neuron*, 14, 941–948 (1995)) are conserved.

Specific examples of DNA of the 4th embodiment of the present invention may include unknown Semaphorin genes which hybridizes under stringent conditions to DNA comprising the nucleotide sequence shown in SEQ ID NO: 7, including all the Semaphorin Z genes of mammal and avian. Between mammals or between mammal and avian, homologous genes have quite similar sequences, and usually more than 75%, in many cases more than 90%, of the base sequence are common each other. Therefore, all the Semaphorin Z genes of mammal and avian are included within the 4th embodiment of the present invention.

The 5th embodiment of the present invention is a protein encoded by DNA of the 4th embodiment of the present invention. Specifically, this embodiment is a protein which is encoded by DNA hybridizing under stringent conditions to DNA comprising the nucleotide sequence shown in SEQ ID NO: 7, and contains Semaphorin domain. These proteins can be expressed and purified by the methods similar to those used for a protein of the 3rd embodiment of the present invention.

These DNAs of the 4th embodiment of the present invention and the proteins of the 5th embodiment of the present invention can be achieved thanks to the discovery of Semaphorin Z which forms the core of the present invention. Once Semaphorin Z has been discovered, one can easily clone DNA of the 4th embodiment of the present invention and express a protein of the 5th embodiment of the present invention, according to conventional methods as described above. Therefore, DNAs of the 4th embodiment of the present invention and proteins of the 5th embodiment of the present invention both of which are found concomitantly with the discovery of Semaphorin Z also retain the essence of the present invention, and are thus included within the scope of the present invention.

The 6th embodiment of the present invention is DNA which encodes a protein inhibiting neurite outgrowth and which hybridizes under stringent conditions to DNA of the 1st embodiment of the present invention (rat and human Semaphorin Z DNA).

The DNA mentioned above hybridizes to DNA shown in SEQ ID NO: 1 or 3, and can be cloned, for example, by screening a cDNA or genomic library prepared from one of various animal tissues using DNA shown in SEQ ID NO: 1 or 3 as a whole or in part as a probe. Particular methods for screening and the like may be similar to those used for DNA of the 4th embodiment of the present invention. The "stringent conditions" used herein may also be similar to those used for DNA of the 4th embodiment of the present invention.

The phrase "inhibiting neurite outgrowth" means that the protein has a collapse activity on growth cone of neuron as demonstrated in Example 8, or that the protein has a neurite-outgrowth inhibition activity. These activities may be measured using, for example, an expression product which is obtained by expressing said DNA by the methods similar to those used for expressing a protein of the 3rd embodiment of the present invention, and, for example, in the following manner:

Since Semaphorin Z is a membrane protein as confirmed in Example 7, activities of Semaphorin Z can easily be measured by using, as a test material, a membrane fraction of cells transformed with Semaphorin Z gene (see Example 8).

Activities of Semaphorin Z can be measured by various methods, and representative methods include, for example, those for a collapse activity on growth cone of neuron (M. Igarashi et al., *Science*, vol. 259, pp. 77–79 (1993)) or a neurite-outgrowth inhibition activity (J. A. Davies et al., *Neuron*, vol. 2, pp. 11–20 (1990); M. Bastmeyer, *J. Neurosci.*, vol. 11, pp. 626–640 (1991)). A method of measuring a growth-cone collapse activity is described in detail in the paper (M. Igarashi et al., *Science*, vol. 259, pp. 77–79 (1993)). Briefly, the measurement may be carried out by a method in which cells expressing Semaphorin Z is homogenized, and the homogenate containing the cell membrane fraction or the purified membrane fraction is used (E. C. Cox et al., *Neuron*, vol. 2, pp. 31–37 (1990)), or by a method in which a protein extracted from the membrane fraction is reconstituted in a liposome and used as a test material (C. E. Bandtlow, *Science*, vol. 259, pp. 80–84 (1993)). To measure a growth-cone collapse activity using these materials, Semaphorin Z protein in one of the foregoing forms is added to neurons cultured under usual conditions (see, for example, "Culturing, Nerve Cells" edited by Banker et al., MIT Press (1991)) in a container coated with a substance promoting the neurite outgrowth and the growth-cone formation, such as laminin, collagen, polylysine or polyornithine. When sufficient time has passed to occur a collapse of growth cone (typically from 30 minutes to one hour after the addition), those neurons are fixed with 1% glutaraldehyde or the like, and the number of the growth cones which have been collapsed is counted under a microscope. In this measurement, it is important that another sample is used as a control, which is prepared from cells not expressing Semaphorin Z according to the completely same procedures as those used for Semaphorin Z-expressing cells. Typically, normalization of the samples is conducted on the basis of the total amounts of protein included within the samples. To measure a neurite-outgrowth inhibition activity, part of the surface of a micropore filter or a culture container made of glass or plastics is coated with Semaphorin Z prepared as described above. The activity may be indicated, for example, by the inability of neurons cultured under usual conditions to adhere to the coated area, or a remarkable decrease in the rate of neurite outgrowth on the coated area, or the inability of invasion of growing neurites from the outside of the coated area into the coated area because of its stopping on the border between the coated and non-coated areas or its avoidance from the coated area. When a cluster of cells expressing Semaphorin Z is co-cultured with neurons in a collagen gel, the inability of outgrowing neurite to enter the cluster of cells expressing Semaphorin Z may also be used as an indicator (A. Sophia et al., *Cell*, vol. 81, 621–629 (1995)).

Specific examples of such DNAs of the 6th embodiment of the present invention, as well as examples of DNAs of the 7th embodiment of the present invention, may include, for example, all the Semaphorin Z genes of mammal and avian.

The 7th embodiment of the present invention is DNA of the 6th embodiment of the present invention which encodes a protein inhibiting neurite outgrowth of CNS-neuron.

In this context, the phrase "inhibiting neurite outgrowth of CNS-neuron" means that the protein has the activity of Semaphorin Z of the present invention, and this activity may be measured by using CNS-neuron as a cell for assay in the measurement described above in connection with the 6th embodiment of the present invention.

As described in the "Prior Art" section, CNS in adult mammals naturally contains a large amount of regeneration (outgrowth) inhibitor. It is, therefore, extremely difficult to measure in vivo an inhibitory effect on neurite outgrowth of CNS-neuron, and such inhibitory effect is usually measured by an in vitro method as described above in connection with the 6th embodiment of the present invention. Since these in vitro methods each have an individual characteristic, it is preferred to use more than one method to confirm the activity. Although preferred neurons used for a measurement of the activity are CNS-neurons such as spinal cord or motor neuron in motor cortex, PNS-neurons in superior cervical ganglion and dorsal root ganglion (DRG) may also be used because NI35/250 known as a CNS-neuron regeneration inhibitor has proved to have neurite-growth inhibition and growth-cone collapse activity also on these PNS-neurons (*J. Cell Biol.*, 106, 1281–1288 (1988), *Science*, 259, 80–83 (1993)).

The 8th embodiment of the present invention is a protein encoded by DNA of the 6th or 7th embodiment of the present invention. Specifically, it is a protein which is encoded by DNA hybridizing under stringent conditions to DNA of the 1st embodiment of the present invention and which protein inhibits neurite outgrowth or which protein inhibits neurite outgrowth of CNS-neuron. These proteins can be expressed and purified by the methods similar to those used for a protein of the 3rd embodiment of the present invention. The activity may be measured by the methods described above in connection with the 6th and 7th embodiments of the present invention.

DNAs of the 6th and 7th embodiments of the present invention and the proteins of the 8th embodiment of the present invention can be achieved entirely thanks to the discovery of Semaphorin Z which forms the core of the present invention. Once Semaphorin Z has been found, one can easily clone and express DNA of the 6th or 7th embodiment of the present invention by conventional methods as described above. The protein of the 8th embodiment of the present invention having said activity can be then identified by subjecting the expression product thus obtained to an activity measurement system as described above. Therefore, DNAs of the 6th and 7th embodiments of the present invention and the proteins of the 8th embodiment of the present invention, both of which are easily found concomitantly with the discovery of Semaphorin Z, also retain the essence of the present invention, and are thus included within the scope of the present invention.

The 9th embodiment of the present invention is DNA which encodes a protein inhibiting neurite outgrowth, said protein containing insertions, deletions, or substitutions of one or more amino acids in the rat and human Semaphorin Zs of the 3rd embodiment of the present invention. The 10th embodiment of the present invention is DNA of the 9th embodiment of the present invention which encodes a protein inhibiting neurite outgrowth of CNS-neuron.

In this connection, one skilled in the art can easily introduce "an insertion, deletion, or substitution of one or more amino acids" by, for example, a site-directed mutagenesis (*Methods in Enzymology*, 100, 448—(1993)) or a PCR method (*Molecular Cloning*, 2nd ed., Chapter 15, Cold Spring Harbor Laboratory Press (1989), "*PCR A Practical Approach*" IRL Press, 200–210 (1991)). The inhibitory effect on neurite outgrowth can be measured by the methods described above in connection with the 6th and 7th embodiments of the present invention.

Based on the structural comparison of known Semaphorins, most of the conserved amino acids are located in Semaphorin domain, suggesting that these conserved amino acids are essential for expression of the activity of Semaphorin. Furthermore, the present inventors has found that a modified Sema III protein in which the aspartic acid residue at position 198 in its Semaphorin domain has been substituted with glycine does not have a growth-cone collapse activity (see Reference example 1 below). Accordingly, the aspartic acid at position 198 of Sema III is believed essential for expression of the activity. The amino acid residues corresponding to this position are highly conserved in known Semaphorins, and they are all aspartic acid with a few exceptions in which glutamic acid is located at this position. It is, therefore, believed that the amino acid residue at this position is also essential for expression of the activity of Semaphorins other than Sema III. In Semaphorin Z of the present invention, the amino acid residue corresponding to the position 198 of Sema III is presumed to be the aspartic acid at position 204 in the amino acid sequence of rat Semaphorin Z shown in SEQ ID NO: 3 or the aspartic acid at position 203 in the amino acid sequence of human Semaphorin Z shown in SEQ ID NO: 4.

Considering the above information, it is desirable to introduce insertions, deletions, or substitutions of one or more amino acids into the amino acid sequence not containing the residues conserved among Semaphorins, so as to retain the activity of Semaphorin Z in the modified protein (a protein encoded by DNA of the 9th or 10th embodiment of the present invention). Particularly, it is desirable not to modify the aspartic acid at position 204 in rat Semaphorin Z shown in SEQ ID NO: 2 and the aspartic acid at position 203 in human Semaphorin Z. In order to substitute an amino acid conserved among Semaphorins while retaining the activity of Semaphorin Z, it is desirable to substitute an amino acid having a similar side chain for the amino acid to be substituted. By substituting such amino acid having a similar side chain for a conserved amino acid, it may be possible to produce a modified protein which has an enhanced activity of Semaphorin Z. Such modified protein having an enhanced activity is highly suitable as a neurite-outgrowth inhibitor for PNS-neuron as will be described below in connection with the 28th embodiment of the present invention.

Figure 2:
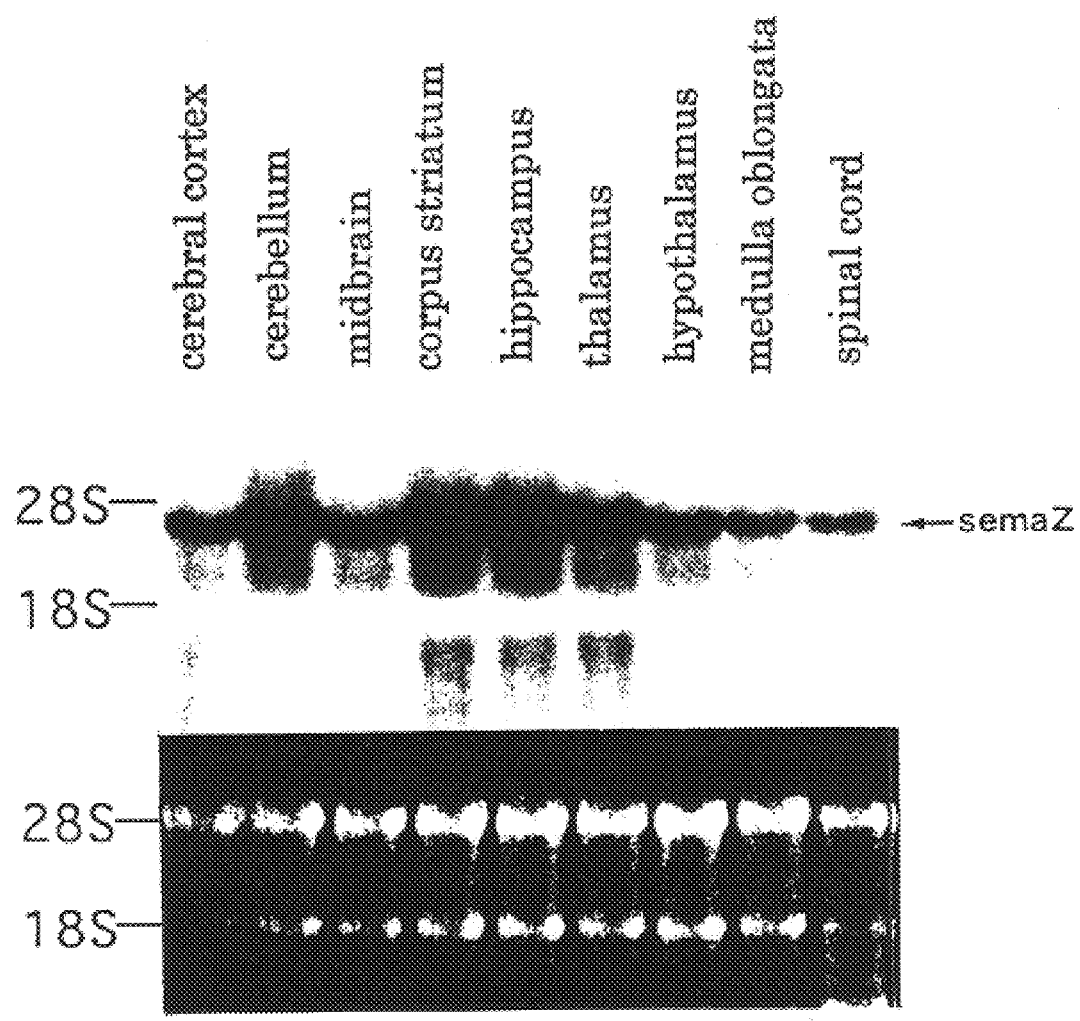

In the above-noted embodiment, "a conserved amino acid" refers to an amino acid located at a position at which more than 50% of Semaphorin genes shown in FIG. 2 of *Cell*, 75, 1389–1399 (1993) or FIG. 1 of *Neuron*, 14, 941–948 (1995) share the same amino acid.

The 11th embodiment of the present invention is a protein encoded by DNA of the 9th or 10th embodiment of the present invention. Specifically, the protein is a so-called "modified protein" which contains insertions, deletions, or substitutions of one or more amino acid in a protein of the 3rd embodiment of the present invention, and which inhibits neurite outgrowth or which inhibits neurite outgrowth of CNS-neuron. These proteins can be expressed and purified by the methods similar to those used for the protein of the 3rd embodiment of the present invention. The activity may be measured by the methods described above in connection with the 6th and 7th embodiments of the present invention.

DNAs of the 9th and 10th embodiments of the present invention and the proteins of the 11th embodiment of the present invention can be achieved entirely thanks to the discovery of Semaphorin Z which forms the core of the present invention. Once Semaphorin Z has been found, one can introduce therein insertions, deletions, or substitutions of one or more amino acids by the conventional methods as described above, and one can identify the protein of the 11th embodiment of the present invention by subjecting the modified protein thus obtained to an activity measurement system as described above. Therefore, DNAs of the 9th and 10th embodiments of the present invention and the proteins of the 11th embodiment of the present invention, both of which are easily attained concomitantly with the discovery of Semaphorin Z, also retain the essence of the present invention, and are thus included within the scope of the present invention.

The 12th embodiment of the present invention is DNA encoding a protein which contains insertions, deletions, or substitutions of one or more amino acids in rat or human Semaphorin of the 3rd embodiment of the present invention, and which protein promotes neurite outgrowth of CNS-neuron.

The insertion, deletion, and substitution in these DNAs can be introduced therein according to the procedures similar to those used for DNA of the 9th embodiment of the present invention. The activity which promotes neurite outgrowth of CNS-neuron can easily be measured by, for example, adding a test material (i.e., a modified Semaphorin Z protein as a candidate) to an assay system for the activity described above in connection with the 6th and 7th embodiments of the present invention. For details, see the descriptions of the 24th embodiment of the present invention.

A specific example of these proteins may be a modified Semaphorin Z protein of which neurite-outgrowth inhibition activity on CNS-neuron has been inactivated. When the modified protein which does not have such inhibition activity binds to a receptor for Semaphorin Z or to Semaphorin Z itself, the neurite-outgrowth promotion effect on CNS-neuron will arise. As described above in connection with the 9th embodiment of the present invention, it has been suggested that the active site of Semaphorin may be located in Semaphorin domain, and particularly, it may be located at the aspartic acid at position 204 in rat Semaphorin Z or the aspartic acid at position 203 in human Semaphorin Z. Accordingly, in order to eliminate the Semaphorin Z activity, it is desirable to conduct insertions, deletions or substitutions of one or more amino acids at the conserved amino acid(s) in said Semaphorin domain, preferably directed to the aspartic acid at position 204 in rat Semaphorin Z or to the aspartic acid at position 203 in human Semaphorin Z. In such cases, those substitutions in which an amino acid having a side chain of a distinct nature is substituted for the original amino acid are desirable.

Since the protein encoded by DNA of the 12th embodiment of the present invention promotes neurite outgrowth of CNS-neuron as described above, it serves as a regeneration promoter for CNS-neuron as described below in connection with the 27th embodiment of the present invention.

The 13th embodiment of the present invention is a protein encoded by DNA of the 12th embodiment of the present invention. Specifically, it is a protein which contains insertions, deletions, or substitutions of one or more amino acids in the protein of the 3rd embodiment of the protein invention, and which promotes neurite outgrowth of CNS-neuron. These proteins can be expressed and purified by the methods similar to those used for the protein of the 3rd embodiment of the present invention. The neurite-outgrowth promotion effect on CNS-neuron may be measured by the methods described above in connection with the 12th embodiment of the present invention.

These DNAs of the 12th embodiment of the present invention and the proteins of the 13th embodiment of the present invention can be achieved entirely thanks to the discovery of Semaphorin Z which forms the core of the present invention. Once Semaphorin Z has been found, one can produce a modified protein in which insertions, deletions, or substitutions have been introduced by the conventional methods as described above, and one can easily identify the modified protein having a neurite-outgrowth promotion activity by subjecting it to a measurement system (screening system) for such activity as described above. DNAs of the 12th embodiment of the present invention and the proteins of the 13th embodiment of the present invention, both of which are easily attained concomitantly with the discovery of Semaphorin Z, also retain the essence of the present invention, and are thus included within the scope of the present invention.

The 14th embodiment of the present invention is DNA which is cloned from a human cDNA or genomic library and which hybridizes under stringent conditions to DNA comprising at least part of rat or human Semaphorin Z DNA of the 1st embodiment of the present invention or at least part of the complementary strand thereof.

Methods of Cloning are described in detail in, for example, "*Molecular Cloning* 2nd ed.", Cold Spring Harbor Laboratory Press (1989), and specifically include, for example, methods employing hybridization or PCR reaction. Although a preferred library used herein is a genomic library derived from human, a cDNA library derived from CNS-neuron in the adult may also be used. Those methods employing hybridization may be carried out according to, for example, *TINS*, 15, 319–323 (1992) and references cited therein. Those methods employing PCR may be carried out according to, for example, "PCR", edited by McPherson et al. ed., 1991, IRL Press.

The DNA thus cloned is a gene for human Semaphorin Z, and such DNAs include not only the full length DNA but also its DNA fragments comprising more than 200 bases. Specific examples of DNA of the 14th embodiment of the present invention may include chromosomal DNAs containing 5' and/or 3' transcriptional control regions, noncoding regions of exons, introns, or the like, in addition to those consisting of a region encoding amino acids. Such sequences which do not encode any amino acids are also quite useful, for example, when it is desired to develop a medicine using antisense techniques described below.

Since these DNAs of the 14th embodiment of the present invention are also easily achieved concomitantly with the discovery of Semaphorin Z, it goes without saying that they are included within the scope of the present invention.

The 15th embodiment of the present invention is an expression plasmid expressing one of DNAs of the 1st, 2nd, 4th, 6th, 7th, 9th, 10th, 12th, and 14th embodiments of the present invention. The 16th embodiment of the present invention is a transformant transformed with said expression plasmid. The 17th embodiment of the present invention is a process for producing a recombinant protein which process is characterized in that it comprises culturing said transformant under conditions in which said expression plasmid can be expressed. As described above in connection with the 3rd embodiment of the present invention, methods of preparing an expression plasmid and a transformant, and methods of producing a recombinant protein, per se, are all well known to those skilled in the art.

The 18th embodiment of the present invention is a polypeptide comprising at least 6 amino acids of one of the proteins of the 3rd, 5th, 8th, 11th, and 13th embodiments of the present invention. In this connection, the limitation "at least 6 amino acids" is based on the fact that a minimal size of polypeptide capable of forming a stable structure consists of 6 amino acids, and preferred polypeptides are those consisting of 10–20 amino acids. A short polypeptide such as those consisting of 10–20 amino acids can be synthesized on a peptide synthesizer, while a longer polypeptide can be obtained by preparing DNA through usual genetic engineering, and expressing it in, for example, an animal cell as described above. The polypeptide thus prepared can also be modified by usual methods.

These polypeptides can be applied to medicaments as described below in connection with the 19th and 20th embodiments of the present invention and can also be used for producing antibodies.

The 19th embodiment of the present invention is a polypeptide of the 18th embodiment of the present invention which promotes neurite outgrowth of CNS-neuron. Such polypeptide may be prepared by the methods described above in connection with the 18th embodiment of the present invention. The promotion effect on neurite outgrowth of CNS-neuron can easily be measured as described above in connection with the 12th embodiment of the present invention by adding a test substance (i.e., a polypeptide derived from Semaphorin Z as a candidate) to an activity measurement system described above in connection with the 6th and 7th embodiments of the present invention. For details, see the descriptions of the 24th embodiment of the present invention.

A specific example of these polypeptides may be a Semaphorin Z polypeptide of which neurite-outgrowth inhibition activity on CNS-neuron has been lost. When a polypeptide which does not have such inhibition activity bind to a receptor for Semaphorin Z or to Semaphorin Z itself, the neurite-outgrowth promotion effect on CNS-neuron will arise. As described below in connection with the 27th embodiment of the present invention, such polypeptide may serve as a CNS-neuron regeneration promoter.

The 20th embodiment of the present invention is a polypeptide of the 18th embodiment of the present invention characterized in that it contains aspartic acid residue at position 203 of the amino acid sequence shown in SEQ ID NO: 4 or an amino acid corresponding to the position of said aspartic acid residue. Such polypeptide may be prepared by the methods described above in connection with the 18th embodiment of the present invention.

As described above in connection with the 9th embodiment of the present inventions, the aspartic acid residue at position 203 of human Semaphorin Z shown in SEQ ID NO: 4 (in the case of rat, the aspartic acid at position 204) seems essential for expression of the activity of Semaphorin Z. Since this amino acid may possibly be involved in the binding between Semaphorin Z and Semaphorin Z receptor, a polypeptide of the 20th embodiment of the present invention containing this amino acid residue may interfere with the neurite-outgrowth inhibition activity on CNS-neuron exerted by Semaphorin Z, by binding to the receptor for Semaphorin Z or to Semaphorin Z itself, resulting in promotion of neurite outgrowth of CNS-neuron. A polypeptide having such effect may serve as a CNS-neuron regeneration promoter as described below in connection with the 27th embodiment of the present invention. Such neurite-outgrowth promotion activity on CNS-neuron can easily be measured as described above in connection with the 12th embodiment of the present invention by adding a test substance (i.e., a polypeptide derived from Semaphorin Z polypeptide as a candidate) to an activity measurement system described above in connection with the 6th and 7th embodiments of the present invention. For details, see the descriptions of the 24th embodiment of the present invention.

In the above-noted embodiment, "an amino acid corresponding to the position of said aspartic acid" refers to an amino acid which is located at the position corresponding to position 203 in human Semaphorin Z, when the amino acid sequence of the protein of the 5th, 8th, 11th, or 13th embodiment of the present invention is aligned with the amino acid sequence shown in SEQ ID NO: 4 so that a maximal identity is obtained. Accordingly, "a polypeptide characterized in that it contains an amino acid corresponding to the position of said aspartic acid" refers to a polypeptide which comprises such amino acid at the position corresponding to position 203 of human Semaphorin Z as well as a few amino acids contiguous to said amino acid.

The 21st embodiment of the present invention is DNA or RNA comprising 8 or more bases, or a chemically modified variant thereof, which has a sequence complementary to one of the DNAs of the 1st, 4th, 6th, 7th, and 14th embodiments of the present invention.

In this context, "DNA or RNA which has a sequence complementary to . . . " (referred to hereinafter as "antisense nucleotide") is a so-called antisense oligonucleotide, antisense RNA, or antisense DNA, and it may be artificially prepared using a DNA synthesizer, or may be obtained by, for example, expressing a gene in the direction opposite to the usual case (i.e., in the antisense direction) as described below in Example 9. For details, see the descriptions of the 27th embodiment of the present invention.

These antisense nucleotides are used for inhibiting the expression of Semaphorin Z as described below in connection with the 22nd embodiment of the present invention. In addition, they are also useful as laboratory reagents for, for instance, in situ hybridization. In this embodiment, "a chemically modified variant" specifically refers to such a variant that is chemically modified so as to enhance the transferability of the antisense oligonucleotide into cells or the stability of the antisense oligonucleotide in the cells. Examples of such chemically modified variant are phosphorothioate, phosphorodithioate, alkylphosphotriester, alkyl phosphonate, alkyl phosphoamidate, and the like derivatives ("*Antisense RNA and DNA*", WILEY-LISS, 1992, pp. 1–50, *J. Med. Chem.*, 36, 1923–1937 (1993)). These chemically modified variant may be prepared according to, for example, the above-mentioned papers.

The 22nd embodiment of the present invention is DNA or RNA of the 21st embodiment of the present invention, or a chemically modified variant thereof, which is characterized in that it inhibits the expression of one of the proteins of the 3rd, 5th, and 8th embodiment of the present invention.

A mRNA produced by usual gene transcription is a sense-strand. The antisense nucleotides, that is, antisense oligonucleotide and antisense DNA or RNA, or chemically modified variants thereof can bind to the sense-strand mRNA in cells to inhibit the expression of that particular gene. Therefore, the above-described antisense nucleotides or chemically modified variants thereof can inhibit the expression of Semaphorin Z of, for example, the 3rd embodiment of the present E-invention, thereby inhibiting the activity of said Semaphorin Z. Antisense nucleotides or chemically modified variants thereof having such effect serve as CNS-neuron regeneration promoters as described below in connection with the 27th embodiment of the present invention.

It can easily be determined whether a particular antisense nucleotide prepared, or a chemically modified variant thereof has a desired inhibitory effect or not, by directly introducing the antisense oligonucleotide itself or, as will be described below in Example 11, introducing a gene which produces said antisense RNA when transcribed, into a cell expressing Semaphorin Z, and then determining whether the amount of the expressed Semaphorin Z is decreased or not.

Examples of an antisense nucleotide exhibiting such inhibitory effect may be those having sequences complementary to the coding region or the 5' or 3' noncoding region of Semaphorin cDNA of the above-described embodiments. Especially preferred are those having sequences complementary to the transcription initiation site, translation initiation site, 5' noncoding region, exon-intron junction region, or 5' CAP region. As described in Example 11, an antisense RNA for Semaphorin Z of the present invention has been confirmed to inhibit the expression of Semaphorin Z. Therefore, it may serve as a CNS-neuron regeneration promoter of the 27th embodiment of the present invention described below.

The 23rd embodiment of the present invention is an antibody against one of the proteins of the 3rd, 5th, 8th, 11th, and 13th embodiments of the present invention or against one of the polypeptides of the 18th–20th embodiments of the present invention. Such antibody can easily be produced by immunizing a mouse or rabbit against a recombinant Semaphorin Z protein of claim 17 or a peptide of claim 18, according to the procedures described in, for example, *Current Protocols in Immunology*, pp. 2.4.1–2.6.6 (1992, J. E. Coligan ed.). Monoclonal antibodies can also easily be produced by the methods described in the above-mentioned reference. Such antibodies may be used in affinity chromatographies or screening of cDNA libraries, and as a pharmaceutical or diagnostic agent, or a laboratory reagent. Some of such antibodies can neutralize the activity of Semaphorin Z. These neutralizing antibodies can easily be identified as described above in connection with the 12th embodiment of the present invention by adding a test substance (i.e., a candidate antibody against Semaphorin Z) to an activity measurement system described above in connection with the 6th and 7th embodiments of the present invention. As described below in connection with the 27th embodiment of the present invention, such neutralizing antibody may serve as a CNS-neuron regeneration promoter.

One skilled in the art can easily prepare the above-described polypeptide of the 18th–20th embodiments of the present invention, DNA or RNA of the 21st or 22nd embodiment of the present invention or chemically modified variant thereof, and the antibody of the 23rd embodiment of the present invention, only if Semaphorin Z has been discovered. In addition, as described above, the state of the art allows one skilled in the art to easily determine whether or not such substances have particular functions such as neurite-outgrowth promotion effect on CNS-neuron. Accordingly, these substances are all included within the scope of the present invention.

The 24th embodiment of the present invention is a screening method for Semaphorin Z inhibitors, which method is characterized in that it employs one of the proteins of the 3rd, 5th, 8th, and 11th embodiments of the present invention. As used herein, "Semaphorin Z inhibitor" refers to a substance which inhibits, for example, the neurite-outgrowth inhibition activity on CNS-neuron exerted by Semaphorin Z.

The screening is conducted by adding a test substance to a Semaphorin Z activity measurement system described above in connection with the 6th and 7th embodiments of the present invention. Specifically, inhibition of the Semaphorin Z activity resulted from the addition of the test substance to the culture medium throughout the incubation period or only temporarily in the incubation period can be used as an indicator in the Semaphorin Z activity measurement. It is also important to confirm that the test substance alone does not influence the survival and neurite-outgrowth of neurons at the same concentration. When both of these requirements are fulfilled, one can consider the test substance as a Semaphorin Z inhibitor. Although it is preferred to prepare in advance the test substance in the form of aqueous solution, an organic solvent such as DMSO may also be used as a solvent. In any cases, it is important to minimize the volume of the solvent so as to exclude any effects of the solvent on neurons. Specifically, the volume to be added should be less than an equal volume, preferably less than 1/10 volume, and more preferably less than 1/100 volume relative to the culture medium. Semaphorin Z inhibitor thus obtained may be used as a CNS-neuron regeneration promoter as described below in connection with the 27th embodiment of the present invention.

The 25th embodiment of the present invention is Semaphorin Z inhibitor which is obtained by the screening method of the 24th embodiment of the present invention. The inhibitor may have any structure and any form, provided that it inhibits the activity of Semaphorin Z.

The 26th embodiment of the present invention is Semaphorin Z inhibitor of the 25th embodiment which comprises the protein of the 13th embodiment of the present invention, the polypeptide of the 19th or 20th embodiment of the present invention, or the antibody of the 23rd embodiment of the present invention. Specifically, it comprises the protein of the 13th embodiment, the polypeptide of the 19th or 20th embodiment, or the antibody of the 23rd embodiment of the present invention which inhibits the activity of Semaphorin Z. The inhibitors can easily be selected by conducting the screening of the 24th embodiment of the present invention, and the inhibitors thus selected may serve as a CNS-neuron regeneration promoter as described below in the 27th embodiment of the present invention.

The 27th embodiment of the present invention is a CNS-neuron regeneration promoter characterized in that it comprises at least one of DNAs or RNAs of the 22nd embodiment of the present invention, or chemically modified variants thereof, or at least one of Semaphorin Z inhibitors of the 25th or 26th embodiment of the present invention. This embodiment relates to the use of substances for "promotion of CNS-neuron regeneration". The following descriptions explain the use, dose and the like, of the substances.

1) Antisense Nucleotide or its Chemically Modified Variant

As described above in connection with the 22nd embodiment of the present invention, the antisense nucleotide of the 22nd embodiment or its chemically modified variant can inhibit the expression of Semaphorin Z gene. Accordingly, such antisense nucleotide may decrease the abundance of the Semaphorin protein, and promote the regeneration of CNS-neuron. Therapeutic methods using the nucleotide or the variant include those in which the antisense oligonucleotide or its chemically modified variant itself is administered, and those in which antisense RNA is produced in cells.

In the method in which the antisense oligonucleotide or its chemically modified variant itself is administered, a preferred antisense oligonucleotide has a length of, for example, about 8–200 bases, and more preferably 8–25 bases, and especially preferably 12–25 bases. Antisense oligonucleotide or its chemically modified variant may be formulated by mixing it with stabilizing agent, buffer, solvent and the like prior to its administration. Such formulation may be co-administered with, for example, an antibiotic, anti-inflammatory, or anesthetic agent. Although the formulation thus prepared may be administered via various routes, it is preferred to topically administered at a site in which neurons are notably disordered. Usually, the regeneration of neuron takes several days to several months, and the formulation is administered every day, or every several days to several weeks. To avoid such frequent administrations, a sustained-release mini-pellet formulation may be prepared and embedded near the affected site. Alternatively, a formulation may be gradually and continuously administered to the affected site by means of, for example, an osmotic pump. Typically, the dose is adjusted so that the concentration at the site of action will be 0.1 nM–10 $\mu$M.

In the method in which an antisense RNA is produced in a cell, a preferred antisense RNA has a length of, for example, more than 100 bases, preferably more than 300 bases, and more preferably more than 500 bases.

The methods by which a gene expressing an antisense RNA is introduced into a patient include an in vivo method in which the gene is directly introduced into a cell in a living body, and an ex vivo method in which the gene is introduced into a particular cell ex vivo and the cell is returned into the body (Nikkei Science, April, 1994, pp. 20–45; Gekkan-Yakuji, 36 (1), 23–48 (1994); Jikkenn-Igaku-Zokan, 12 (15), 1994; and references cited therein). An in vivo method is more preferred.

Such in vivo methods include a method employing recombinant viruses and other methods (Nikkei Science, April, 1994, pp. 20–45; Gekkan-Yakuji, 36 (1), 23–48 (1994); Jikken-Igaku-Zokan, 12 (15), in its entirety (1994); and references cited therein).

The methods employing recombinant viruses may include the methods in which Semaphorin gene is incorporated into a virus genome of, for example, retrovirus, adenovirus, adeno-associated virus (AAV), herpesvirus, vaccinia virus, poliovirus, or sindbis virus, and the virus is introduced into a living body. Among these methods, those employing retrovirus, adenovirus or adeno-associated virus are particularly preferred.

Other methods may include a liposome method or a lipofectin method. The liposome method is particularly preferred.

The ex vivo methods which may be used include, besides those described above, a micro-injection method, a calcium phosphate method, electroporation and the like.

Administration of the gene to a patient is carried out via appropriate routes depending on particular disease or symptom to be treated, and the like. For example, it may be administered intravenously, intraarterially, subcutaneously, or intramuscularly, or directly administered into an affected site such as neuron. For example, when spinal cord is infected with the recombinant viruses, the expression of Semaphorin gene is inhibited exclusively in the spinal cord. Usually, the expression of antisense RNA lasts several days to several months, and such single infection is sufficient to allow the regeneration of neuron. When expressed insufficiently, the gene may be re-introduced. When administered by an in vivo method, the gene may be formulated in the form of, for example, a solution, and typically it is formulated in the form of an injection containing Semaphorin gene as an active ingredient to which conventional carrier and the like may be added, if necessary. In the case of liposomes or membrane-fused liposomes (such as Sendai virus (HVJ)-liposomes) containing Semaphorin gene, the liposome preparations may be in the form of a suspension, a frozen preparation, a centrifugally-concentrated frozen preparation or the like.

Although the amount of Semaphorin gene in the formulation may vary depending on the disease to be treated, the age and weight of the patient, and the like, it is typically 0.0001–100 mg, and preferably 0.001–10 mg, and such formulation is preferably administered once every several days to several months.

2) Modified Protein of Semaphorin Z

As described above in connection with 12th and 13th embodiments of the present invention, one can prepare a modified Semaphorin Z protein in which the neurite-outgrowth inhibition activity on CNS-neuron has been abolished. When administered into a living body, such modified protein may bind to receptors for Semaphorin Z or to Semaphorin Z itself, resulting in an inhibition of the Semaphorin Z activity and a promotion of the regeneration of CNS-neuron.

Such modified protein of Semaphorin Z is formulated with a stabilizer, buffer, and diluent, and administered to a patient for therapy. Such formulation may be administer by any one of various routes, and it is preferred to topically administer to the focal site. Since regeneration of neuron usually takes several days to several months, the formulation is administered once or more in order to continuously inhibit the Semaphorin Z activity throughout the period. When administered more than once, it is desirable to administer it every day or repeatedly at appropriate intervals. When administered to CNS by injection, for example, into spinal cord, several hundreds μg to 2 g, preferably less than several tens mg, are used per administration. To reduce the administration frequency, it may be administered using a sustained-release formulation or gradually administered over a long period by means of, for example, an osmotic pump. Alternatively, it may be S administered by grafting into a living body a cell expressing such modified Semaphorin Z protein.

3) Polypeptide Derived from Semaphorin Z

The peptide of the 19th or 20th embodiment of the present invention may suppress the inhibition activity of Semaphorin Z on neurite outgrowth of CNS-neuron by binding to receptors for Semaphorin Z, resulting in a promotion of regeneration of CNS-neuron. As described above in connection with the 20th embodiment of the present invention, polypeptides having such effect include, for example, a polypeptide characterized in that it contains the aspartic acid at position 203 of human Semaphorin Z shown in SEQ ID NO: 4 or an amino acid residue corresponding to said aspartic acid. The suppression may be any one of competitive, noncompetitive, uncompetitive, and allosteric inhibitions.

As for the methods of formulating or administering such polypeptides, and their doses, see the above section “2) Modified protein of Semaphorin Z”.

4) Antibody Against Semaphorin Z

A neutralizing antibody which neutralizes the activity of Semaphorin Z may suppress, when administered into a living body, the activity of Semaphorin Z, and promote the regeneration of CNS-neuron.

The methods of formulating or administering such neutralizing antibody and their doses may be the same as described in the above section “2) Modified protein of Semaphorin Z”. Alternatively, a method in which cells producing a monoclonal antibody are grafted directly into CNS may also be used.

The above-described screening method of the 24th embodiment of the present invention can be established only after the discovery of Semaphorin Z, a representative protein of the present invention which inhibits neurite outgrowth of CNS-neuron. Once Semaphorin Z has been found, one can easily carry out the screening by using the method as described above. By carrying out such screening, one can easily select Semaphorin Z inhibitor of the 25th or 26th embodiment of the present invention which inhibits the neurite-outgrowth inhibition activity on CNS-neuron exerted by Semaphorin Z. Then, such inhibitor, or an antisense DNA or RNA, or its chemically modified variant, as described above which controls the expression of Semaphorin Z is used as a curative ingredient to formulate a CNS-neuron regeneration promoter of the 27th embodiment of the present invention. Therefore, these are all achieved concomitantly with the discovery of Semaphorin Z, and are all included within the scope of the present invention.

The 28th embodiment of the present invention is a neurite-outgrowth inhibitor for PNS-neuron characterized in that it contains at least one of the proteins of the 3rd, 5th, 8th and 11th embodiments of the present invention. Although the proteins of these embodiments inhibit the neurite outgrowth of CNS-neuron, they are also expected to inhibit the neurite outgrowth of PNS-neuron, since PNS-neuron also probably expresses a receptor for Semaphorin Z, and receptors for other Semaphorins also probably react with Semaphorin Z. Accordingly, they may serve as a therapeutic agent for pain or an immune disease such as atopic dermatitis, by virtue of their inhibition activity on neurite outgrowth of PNS-neuron.

As for the methods of formulating or administering such proteins, and their dose, see the above section "2) Modified protein of Semaphorin Z".

The 29th embodiment of the present invention is a transgenic animal in which the DNA of the 1st, 4th, 6th, 7th, 9th, 10th or 12th embodiment of the present invention has been artificially inserted into its chromosome, or has been knocked out.

As apparent from the following references, one skilled in the art can quite easily produce a transgenic animal which has the gene of the 1st, 4th, 6th, 7th, 9th, 10th or 12th embodiment of the present invention inserted into its chromosome, on the basis of the gene information on Semaphorin Z of the present invention (*Manipulation of Mouse Embryo*, B. Hogan et al. ed., 1986, Cold Spring Harbor Laboratory; Shinichi Aizawa, *Gene Targeting*, 1995, Yodosha, etc.). Accordingly, the transgenic animal thus produced is naturally included within the scope of the present invention. The transgenic animal thus produced is very useful as an animal model for developing pharmaceuticals or an animal used for screening of pharmaceuticals. Furthermore, a so-called knockout animal in which the gene of the 1st, 6th or 7th embodiment of the present invention has been deleted at the chromosomal level is characterized in that it does not contain such gene. As described in literatures, or as apparent from the common knowledge in the art, such knockout animals cannot be produced without the gene information on Semaphorin Z of the present invention. It goes without saying, therefore, that such knockout animals are included within the scope of the present invention.

While Semaphorin Z plays an important role in inhibiting the neurite outgrowth of CNS-neuron in vivo as described above, it has been also suggested that Semaphorin gene may have other unknown functions such as immunosuppression (*Cell*, 75, 1389–1399 (1993)). Accordingly, it is quite important to investigate the expression of Semaphorin Z gene or the distribution and function of Semaphorin Z protein for studying this technical field or for diagnosing a patient, for example, with a neural disease. The present invention can provide a gene probe, an antibody, a recombinant protein, a transgenic animal and the like which are useful for such purposes.

BRIEF DESCRIPTION OF DRAWINGS

FIG. 1 shows the result of Northern analysis, indicating distribution of Semaphorin Z expression in adult rat tissues.

RNAs were extracted from various tissues of adult rat, separated by an agarose gel electrophoresis, blotted onto a filter, and hybridized with a $^{32}$P-labeled probe. The upper panel shows the autoradiogram, and the lower panel shows the ethidium bromide staining of the gel after electrophoresis. The positions corresponding to 28S and 18S rRNAs are indicated at the left margin, and the position corresponding to Semaphorin Z mRNA is indicated at the right margin. 15 $\mu$g of RNA was loaded in each lane.

FIG. 2 shows the result of Northern analysis, indicating distribution of Semaphorin Z expression in central nervous tissues.

RNAs were extracted from nine sections of central nervous tissue, separated by an agarose gel electrophoresis, blotted onto a filter, and hybridized with a $^{32}$P-labeled probe. The upper panel shows the autoradiogram, and the lower panel shows the ethidium bromide staining of the gel after electrophoresis. The positions corresponding to 28S and 18S rRNAs are indicated at the left margin, and the position corresponding to Semaphorin Z mRNA is indicated at the right margin. 15 $\mu$g of RNA was loaded in each lane.

FIG. 3 shows the result of Northern analysis, indicating the change in the amounts of Semaphorin Z expression from embryo to adult.

RNAs were extracted from rat tissues at various ages, separated by an agarose gel electrophoresis, blotted onto a filter, and hybridized with a $^{32}$P-labeled probe. The upper panel shows the autoradiogram, and the lower panel shows the ethidium bromide staining of the gel after electrophoresis. RNAs were prepared from the whole embryo at embryonic-day 12 (E12), from the head and the body in the case of embryo at E15, E18 and neonate, and from the whole brain in the adult. The positions corresponding to 28S and 18S rRNAs are indicated at the left margin, and the position corresponding to Semaphorin Z mRNA is indicated at the right margin. 15 $\mu$g RNA was loaded in each lane.

FIG. 4 shows the result of SDS-PAGE, indicating the expression of Semaphorin Z extracellular domain (rSZexII) in *Escherichia coli.*

The left panel shows the induced expression of the extracellular domain (rSZexII) in *E. coli* BL21(DE3)pLysS transformed with a Semaphorin Z partial peptide expression plasmid (pRSZexII). This *E. coli* was cultured, and when turbidity (O.D. 600) of the culture reached 0.4–0.6, IPTG was added at a final concentration of 1 mM to induce the expression. The numerals at the top of the panel indicate the time after the IPTG addition. At the indicated times, the culture was sampled. The cells collected by centrifugation were suspended in a SDS-PAGE sample buffer, and after heat denaturation, separated by SDS-PAGE. The expression of rSZexII (arrow) was observed one hour after the induction, and the amount of expression was increased thereafter. The right panel shows the result of SDS-PAGE of rSZexII purified on a nickel affinity column. Lane M indicates the molecular weight markers, and the numerals at the left margin of the figure each indicate the molecular weight (kD: kiloDalton) of the markers.

FIG. 5 shows the result of SDS-PAGE, indicating the expression of the Semaphorin Z cytoplasmic domain (rSZinc) in *E. coli.*

The left panel shows the induced expression of Semaphorin Z cytoplasmic domain (rSZinc) in *E. coli* BL21(DE3) pLysS transformed with a Semaphorin Z partial peptide expression plasmid (pRSZinc). This *E. coli* was cultured, and when turbidity (O.D. 600) of the culture reached 0.4–0.6, IPTG was added at a final concentration of 1 mM to induce the expression. The numerals at the top of the panel indicate the time after the IPTG addition. At the indicated times, the culture was sampled. The cells collected by centrifugation were suspended in a SDS-PAGE sample buffer, and after heat denaturation, separated by SDS-PAGE. The expression of rSZinc (arrow) was appeared 4 hours after the induction, and the amount of expression was increased after 12 hours. The right panel shows the result of SDS-PAGE of rSZinc purified on a nickel affinity column. Lane M indicates the molecular weight markers, and the numerals at the left margin of the figure each indicate the molecular weight (kD: kiloDalton) of the markers.

FIG. 6 shows the result of Western blotting of Semaphorin Z protein expressed in COS cells.

The left panel: COS cells were transfected with (A) antisense-Semaphorin Z gene expression plasmid pUCSRαSZ(-) or (S) Semaphorin Z expression plasmid pUCSRαSZ. After two days, the membrane fraction and the cytoplasmic fraction were separated, subjected to SDS-PAGE, and then to Western blotting using an anti-Semaphorin Z antibody. (C) indicates a mock transfection. The position corresponding to the Semaphorin Z protein band is indicated at the left margin of the figure. The right panel: the membrane fraction prepared above was treated (Lane (+)) with a glycosidase, N-glycosidase-F, and then analyzed by Western blotting as in the case of the left panel. Lane (-) indicates the result of the same procedure with the exception that the enzyme was not added. The position of Semaphorin Z band is indicated at the right margin of the figure. MW indicates molecular weight makers.

Figure 7:
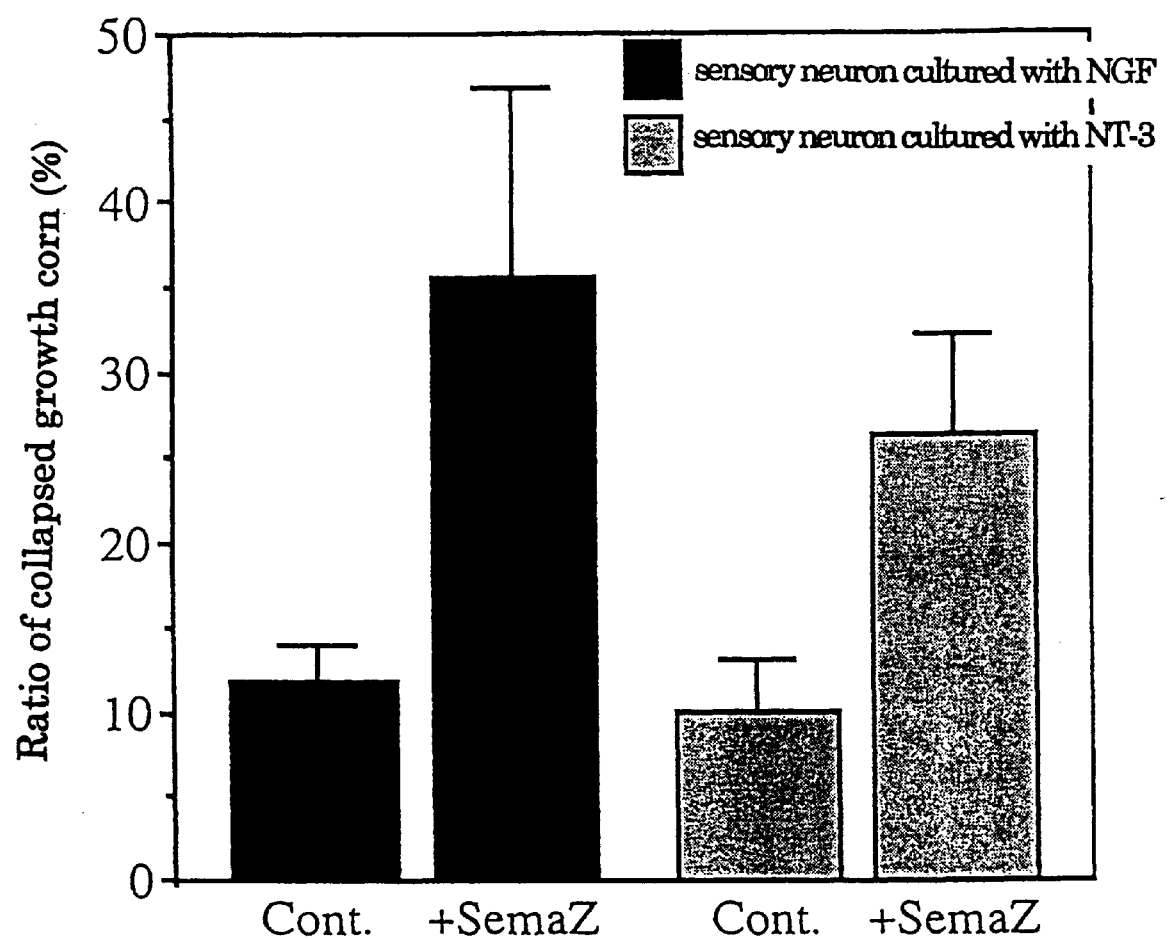

FIG. 7 shows the growth-cone collapse activity of a cell extract prepared from Semaphorin Z-expressing cells.

The extract was prepared from COS 7 cells into which a Semaphorin Z expression plasmid (pAx1CAsemaZ-L) has been introduced (+SemaZ). The extract was then added to chicken embryo dorsal root ganglion neuron cultured in the presence of NGF or NT-3, and the ratio (%) of the neurite having collapsed growth cone was determined. As a control, an extract prepared from cells into which a plasmid expressing an antisense-Semaphorin Z gene (pAx1CAsemaZ-R) has been introduced was used. The value indicated in the figure is the average of the values obtained from 8 ganglions. Standard deviations are shown in the figure.

Figure 8:
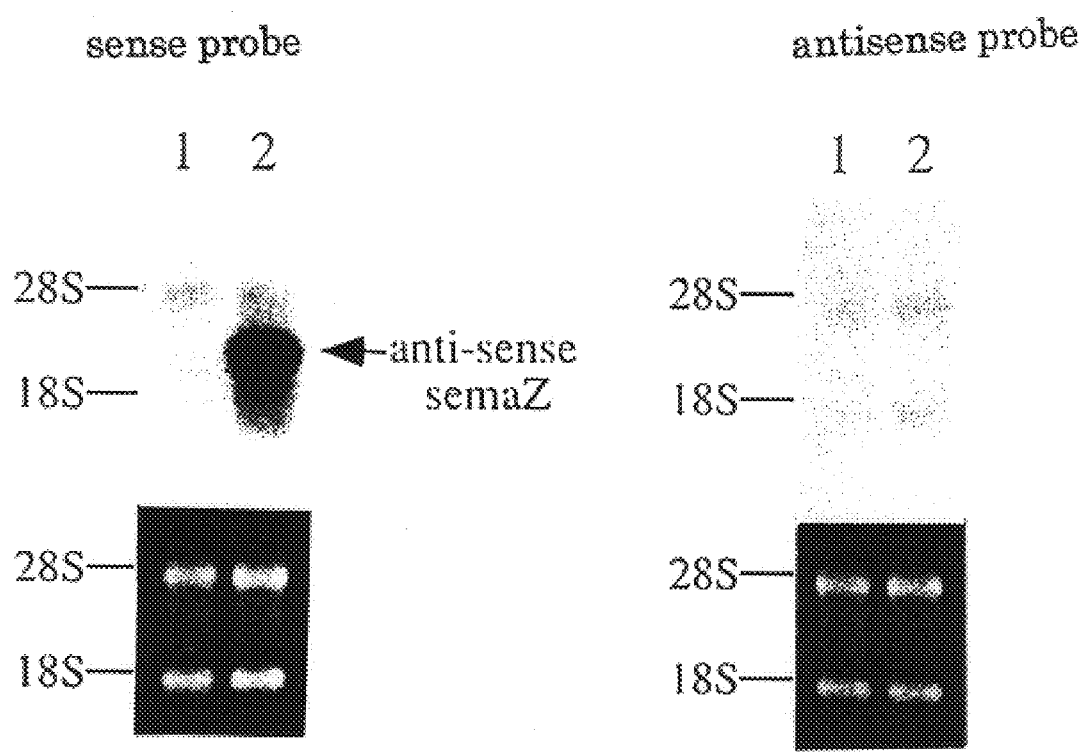

FIG. 8 shows the result of electrophoresis, indicating the expression of antisense-Semaphorin mRNA in cells infected with an antisense-adenovirus.

COS 7 cells were infected with an adenovirus expressing antisense-Semaphorin Z gene (antisense-adenovirus: Ax1CAsemaZ-R) or an adenovirus having no Semaphorin Z gene (control-adenovirus: Ax1CAwt), and after two days, the total RNA was prepared. Five pg of the total RNA was electrophoresed on 1% agarose-formaldehyde gel, blotted onto a membrane filter, hybridized with a sense (left panel) or antisense (right panel) cRNA probe labeled with $^{32}$P, and subjected to autoragiography (the upper panels: autoradiogram). Lane 1 and Lane 2 in each figures respectively indicate the results with RNA prepared from the cells infected with the control-adenovirus or antisense-adenovirus. Antisense-Semaphorin Z mRNA was detected using the sense probe only in the cells infected with the antisense-adenovirus (arrow in the left panel: anti-sense semaZ). The lower panels in each figures indicate the ethidium bromide staining of the electrophoresed gels. The positions of 28S and 18S ribosomal RNAs are indicated at the left margin of the figure.

Figure 9:
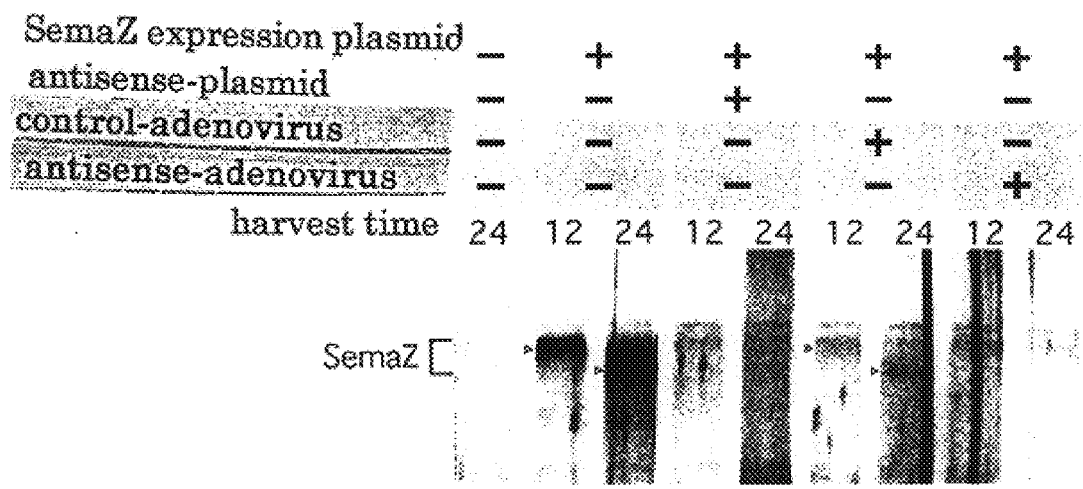

FIG. 9 shows the result of Western blotting, indicating the expression inhibition of Semaphorin Z protein by an antisense-Semaphorin Z gene.

Semaphorin Z expression plasmid (SemaZ expression plasmid, pAX1CASemaZ-L), an antisense-Semaphorin Z expression plasmid (antisense plasmid, pAxCASemaZ-R), an adenovirus having no Semaphorin Z gene (control-adenovirus, AX1CAwt), and an adenovirus expressing an antisense-Semaphorin Z gene (antisense-adenovirus, Ax1CASemaZ-R) were introduced into COS cells in the indicated combinations. After a certain period, the cells were harvested, and the membrane fraction was prepared. The membrane fraction was separated by SDS-PAGE, and then subjected to Western blotting using an anti-Semaphorin Z antibody. The time when Semaphorin Z expression plasmid is transfected was defined as 0 hour, and cells were harvested after 12 and 24 hours. Infection with adenovirus was performed 24 hours before the transfection with the plasmid. The position of Semaphorin Z band is indicated at the left margin of the figure, and also indicated by a triangle at the side of each lanes.

Figure 10:
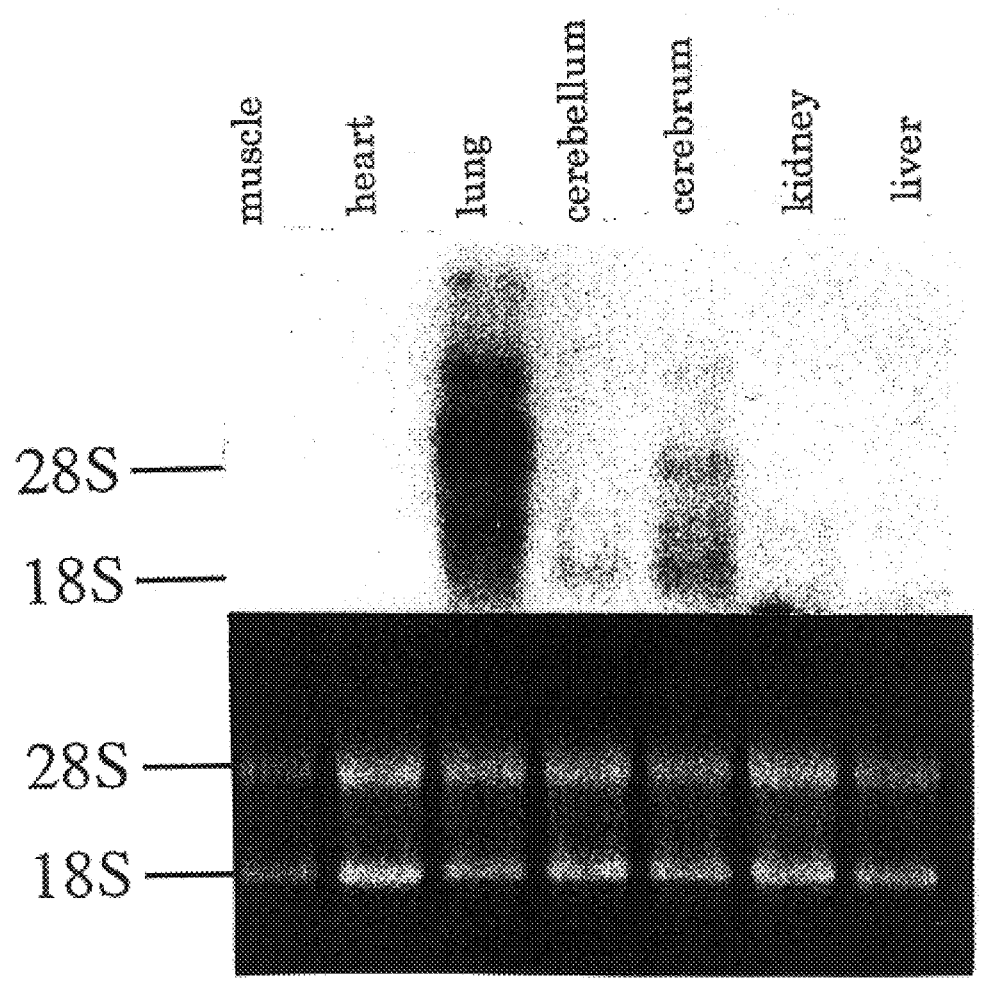

FIG. 10 shows the result of Northern analysis, indicating distribution of Semaphorin III expression in various tissues in vivo.

To determine the distribution of expressed Semaphorin III, the total RNAs were extracted from various tissues in adult rat, electrophoresed on 1% agarose-formaldehyde gel, blotted onto a filter, and hybridized with a mouse Semaphorin III DNA probe labeled with $^{32}$P. The lanes each contained 15 µg RNA. The upper panel indicates the result of autoragiography. The positions of 18S and 28S ribosomal RNAs are indicated at the left margin of the figure. The lower panel indicates the ethidium bromide staining of the gel. The upper band and the lower band in the panel respectively correspond to 28S and 18S ribosomal RNAs.

EXAMPLES

Fundamental procedures for experiments are described in detail in many publications such as *Molecular Cloning*, 2nd Ed. (Maniatis et al. ed., Cold Spring Harbor Laboratory Press, 1989), *Current Protocols in Molecular Biology* (Ausubel et al. ed., John Wiley & Sons, 1987), and *Saibo-Kogaku-Jikken Protocols* (edited by Department of Oncology, The Institute of Medical Science, The University of Tokyo, Shujunsha, 1991). The present invention is not intended to be limited by the following examples, and the examples may be of course modified as usual.

Example 1

Cloning of Rat Semaphorin Z Gene (1) Search Through Database for a Novel Semaphorin Gene Using the dbEST database of the National Center for Biotechnology Research (Bethesda, Md., U.S.), search was performed for a sequence which encodes an amino acid sequence relatively well conserved in known Semaphorin genes and which is found in only cDNAs from postnatal brain but not in cDNAs from fetus. As a result, the nucleotide sequence of File No. T08532 proved to have a sequence (Gln-Asp-Pro-Tyr-Cys-Gly-Trp-Ala SEQ ID NO:5)) which is similar to the sequence of 8 amino acids common to known Semaphorin genes (Gln (or Arg)-Asp-Pro-Tyr (or His)-Cys-Ala (or Gly)-Trp-Asp SEQ ID NO:6)). However, the sequence information of T08532 consisting of 176 bases is so short compared with the cDNAs for known Semaphorin genes, and only about 10% of the total nucleotides could be translated to a sequence common to those in known Semaphorins. In addition, the reading frame could not be determined because the sequence of T08532 is not the one finally determined. It was, therefore, impossible to conclude that the sequence is part of a novel Semaphorin gene. Thus, the present inventors adopted the following strategy. Firstly, we confirmed that a gene containing the above sequence was expressed in adult brain, which is required for the aim of the present invention. The full length cDNA containing the above sequence was then cloned, and the structure of the gene was determined to judge whether or not it corresponds to a novel Semaphorin.

(2) Confirmation of the Expression of the Gene Containing the Sequence of T08532 in the Brain To confirm that the gene is expressed in adult human CNS, two DNA primers (5'-AAGATGCAGGAGCCGTCG- 3' (SEQ ID NO: 8), and 5'-CAGCGGCTGCTGAGCTTG-3' (SEQ ID NO: 9)) were synthesized on the basis of the nucleotide sequences at each end of T08532, and used in a PCR reaction under usual conditions together with cDNAs prepared from a human hippocampal cDNA library (Stratagene) as a template. As a result, about 170 bp fragment approximately equal to total-length of T08532 was amplified. To confirm that the fragment has the same base sequence as that of T08532, the DNA was then cloned into pCRII (Invitrogen) according to the protocol supplied by Invitrogen, and the total nucleotide sequence was determined. More than 95% of the sequence thus obtained (SEQ ID NO: 7) coincided with that of T08532, confirming that a gene containing the sequence of T08532 is expressed in the adult human brain.

(3) Isolation of Rat Semaphorin Z Gene

Then, the inventors have decided to clone the full-length of the gene to determine whether or not the gene corresponds to a novel Semaphorin. Since it is expected that in the subsequent research, a rat gene preparation may be more easily accessible than a human gene, the rat gene was firstly cloned. Specific procedures for such cloning are as follows.

Firstly, the 176 bp CDNA fragment (SEQ ID NO: 7) obtained in the above section (2) was used as a probe to screen a cDNA library in the following manner. The cDNA library was prepared by the conventional method described in the above-mentioned laboratory manuals using mRNA prepared from rat brain by the conventional method and Lambda Zap II (λZapII) CDNA Library Preparation Kit (Stratagene) to obtain about 150 thousand plaques. These plaques were transferred onto a nylon membrane (Nippon Pall). The DNAs were denatured, neutralized, fixed with ultraviolet rays of 0.6 J/cm$^2$, and then used in a hybridization. The hybridization was conducted at 42° C. for 48 hours by adding the nylon membrane and the 176 bp DNA fragment labeled with $^{32}$P (prepared using Megaprime DNA Labeling System (Amersham)) as a probe to a hybridization buffer (45% (v/v) formamide, 5×SSPE (1×SSPE consists of 0.15 M sodium chloride, 10 mM sodium dihydrogenphosphate, and 1 mM disodium ethylenediaminetetraacetate, adjusted to pH 7.0), 2×Denhardt's solution (Wako Pure Chemical Industries), 0.5% (w/v) sodium dodecyl sulfate (SDS), 20 μg/ml salmon sperm DNA (Wako Pure Chemical Industries)). After the reaction, the nylon membrane was washed 2–3 times in 2×SSPE, 0.5% (w/v) SDS at room temperature for 10 min, and further washed 2–3 times in 2×SSPE, 0.5% (w/v) SDS at 42° C. for 10 min. The filters thus prepared were analyzed using BAS 2000 Bio Image Analyzer (Fuji Film), and 4 positive signals were obtained. Plaques corresponding to the positive signals were excised from the agarose plate, placed in 500 μl of SM buffer (100 mM sodium chloride, 15 mM magnesium sulfate, 50 mM Tris (pH 7.5), 0.01% gelatin) supplemented with 20 μl of chloroform, and left overnight at 4° C. to elute the phages. The recombinant lambda phages thus obtained were subjected to a secondary screening according to the procedures as described above, and single plaques were isolated. The phages thus obtained were treated in the following manner for in vivo excision of a phagemid containing the cDNA insert, according to the protocols supplied by Stratagene. Agarose gels containing the 4 single plaques obtained in the secondary screening were each placed in 500 μl of SM buffer, supplemented with 20 μl of chloroform, and then allowed to stand overnight at 4° C. Two hundred fifty μl of the phage solution obtained, 200 μl of E. coli XL-1 Blue MRF' suspended in 10 mM magnesium chloride at $OD_{600}$=1.0, and 1 μl of ExAssist helper phage (>1×10$^6$ pfu/ml) were mixed, and incubated at 37° C. for 15 min. Then, 3 ml of LB medium (prepared by mixing 0.5% (w/v) sodium chloride, 1% (w/v) Bactotrypton (Difco), and 0.5% (w/v) yeast extract (Difco) and the mixture was then adjusting to pH 7.0 using 5 M sodium hydroxide) was added, and the mixture was shaken at 37° C. for 2–3 hours. The cells were removed by centrifuging at 2000×g for 15 min, and the supernatant was treated at 70° C. for 15 min. The supernatant was then centrifuged again at 2000×g for 15 min, and the supernatant was recovered as a stock solution of a phagemid containing the cDNA insert. An aliquot (10–100 μl) of the phagemid stock solution was mixed with 200 μl of E. coli SOLR ($OD_{600}$=1.0), incubated at 37° C. for 15 min, and 10–50 μl of the mixture was then plated onto an ampicillin plate, incubated overnight at 37° C. to obtain E. coli strain containing a double stranded phagemid into which the gene fragment of interest has been inserted.

(4) DNA Sequencing

The nucleotide sequence of the cDNA clone obtained was analyzed on Model 377 DNA Sequencer (Perkin-Elmer) to determine the total nucleotide sequence. The reaction was carried out using PRISM Dye termination kit (Perkin-Elmer). The DNA nucleotide sequence thus determined (3692 bases), the putative open reading frame (2664 bases), and the amino acid sequence (887 amino acids) are shown in SEQ ID NO:1, residues 19 through 2682 of SEQ ID NO:1, and SEQ ID NO:2, respectively.

By comparing the sequence of the gene with known sequences in database, the gene has proved to be a novel gene. Furthermore, it was definitely confirmed that it is a novel protein belonging to the Semaphorin family, since the region from position 49 to position 580 of the amino acid sequence has a homology to the so-called Semaphorin domain sequence, and 12 cysteins among 13 cysteines highly found among Semaphorin genes are conserved also in the novel sequence. Thus, the novel protein was designated Semaphorin Z.

Example 2

Cloning of Human Semaphorin Z Gene

Two primers (5'-TACTTCAATGTACTGCAGGCT-3' (SEQ ID NO: 10) and 5'-AAGATGCAGGAGCCATCGGGG-3' (SEQ ID NO: 11)) were synthesized on the basis of the nucleotide sequence of rat Semaphorin Z obtained in Example 1, and used in a PCR reaction together with cDNAs prepared from a human frontal lobe cortex cDNA library (Stratagene) as a template to amplify a cDNA fragment corresponding to human Semaphorin Z. The amplified fragment was cloned into pCRII (Invitrogen), and the nucleotide sequence was determined as described in Example 1. To exclude any errors during the PCR reaction, the nucleotide sequences of 4 independent clones were compared, and the correct sequence was determined.

Apart from the above, the sequence of rat Semaphorin Z was compared with sequences in EST database (dbEST) using a homology analysis program, blastn, in order to find an EST clone encoding the DNA sequence of human Semaphorin Z. As a result, z45909 has proved to have a sequence highly similar to that of rat Semaphorin Z. Accordingly, an EST clone-containing this sequence (ID#184382) was purchased from Genome Systems Inc. (U.S.), and the total base sequence was determined by the method described in Example 1.

For a region of which nucleotide sequence could not be determined by such two methods, a human forebrain cDNA library was repeatedly screened using a rat Semaphorin gene fragment corresponding to such undetermined human region as a probe. In this manner, the nucleotide sequence encoding the full-length human Semaphorin Z was finally determined. The DNA nucleotide sequence thus determined (3524 bases), the putative open reading frame (2667 bases), and the amino acid sequence (888 amino acids) are shown in SEQ ID NO:3, residues 39 through 2702 of SEQ ID NO:3, and SEQ ID NO:4, respectively. The amino acid sequence shown in SEQ ID NO: 4 has proved to represent human Semaphorin Z, since it showed 89% identity with the amino acid sequence of rat Semaphorin Z shown in SEQ ID NO: 2.

Example 3

Tissue-specific Gene Expression of Semaphorin Z Confirmed by Northern Analysis (1) Preparation of RNA Various tissues were excised from rat, and RNAs were prepared therefrom by AGPC method (Takashi Tuji and Toshikazu Nakamura, *Jikken-Igaku*, vol. 9, 1991, pp. 1937–1940; M. F. Ausubel et al. ed., *Current Protocols in Molecular Biology*, 1989, pp. 4.2.4–4.2.8, Greene Pub. Associates & Wiley-Interscience). Briefly, 10 ml of a denaturing solution (4M guanidine thiocyanate, 25 mM sodium citrate (pH 7.0), 0.5% sarkosyl, 0.1 M 2-mercaptoethanol) was added to each 1 g of excised tissue, and quickly homogenized using a Polytron homogenizer. To the homogenate, 0.1 volume of 2 M sodium acetate (pH 4.0), 1 volume of water-saturated phenol, and 0.2 volumes of chloroform-isoamyl alcohol (49:1) were added, and the mixture was vigorously stirred. After centrifugation, the aqueous layer was isolated, an equal volume of isopropyl alcohol was added thereto, and the mixture was allowed to stand at $-20°$ C. for 1 hour. The precipitate was recovered by centrifugation, and dissolved again in 2–3 ml of the denaturing solution per 1 g tissue. An equal volume of isopropyl alcohol was added, and the mixture was allowed to stand at $-20°$ C. for 1 hour, and then RNA was centrifuged. The precipitate was washed with 75% ethyl alcohol, briefly dried, and then dissolved in an appropriate amount of water.

(2) Electrophoresis and Northern blotting of RNA Electrophoresis and Northern blotting of RNA were performed according to *Molecular Cloning* 2nd Ed. (Maniatis et al. ed., Cold Spring Harbor Laboratory Press (1989)). Briefly, RNAs prepared from various tissues were electrophoresed on 1% agarose gel containing formaldehyde. The gel was shaken in 50 mM NaOH for 20 min, and then in 10×SSPE for 40 min. The RNAs were then blotted onto a nylon membrane (Biodyne B, Nippon Pall) by means of capillary transfer, and fixed using an UV cross-linker (Stratagene) (0.6 J/cm$^2$).

(3) Hybridization

Using two primers (5'-CAGGAACACGAACCACAC-3' (SEQ ID NO: 12) and 5'-GTATGCAAGAATGATGTG-3' (SEQ ID NO: 13)), PCR reaction was carried out with rat Semaphorin Z cDNA as template to obtain a fragment of 775 bp. This DNA fragment was labeled with $^{32}$P as described in Example 1, and used as a probe. Hybridization was carried out at 42° C. for 16–24 hours by incubating the nylon membrane on which RNAs have been blotted with the DNA probe in a hybridization buffer same as that described in Example 1. After the reaction, the nylon membrane was washed 2–3 times in 2×SSPE, 0.5% (w/v) SDS for 10 min at room temperature, and further washed 2–3 times in 2×SSPE, 0.5% SDS (w/v) at 65° C. for 20 min. The filter thus prepared was subjected to autoragiography for analysis.

(4) Results

Figure 3:
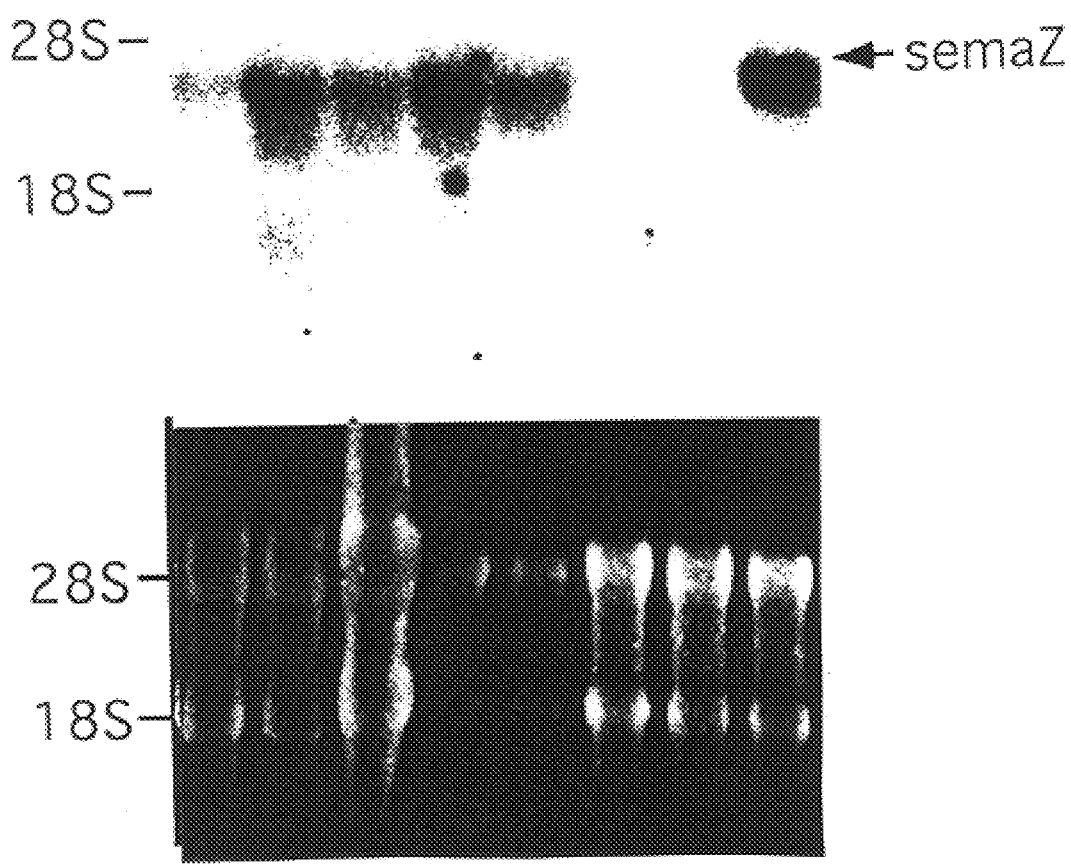

As shown in FIG. 1, mRNA of Semaphorin Z was highly expressed in adult CNS (cerebrum, cerebellum), whereas it was scarcely expressed in peripheral tissues except for spleen. Furthermore, as shown in FIG. 2, Semaphorin Z of the present invention was expressed throughout the entire tissues of CNS, although particularly high expression was observed in cerebellum, hippocampus, and corpus striatum. In addition, as shown in FIG. 3, the expression of Semaphorin Z mRNA was very weak in embryos, and in particular the expression was hardly observed in an embryonic-day 12 embryo (E12 embryo), and a newborn rat.

As mentioned above, Semaphorin Z of the present invention has the characteristics that 1) it is highly expressed in adult CNS in general and 2) it is poorly expressed in embryos or peripheral tissues in the adult where the neurite outgrowth is not inhibited. It was thus demonstrated that Semaphorin Z of the present invention exhibits an expression distribution which may be considered as typical of a "CNS-neuron regeneration inhibitor".

Example 4

Expression of Semaphorin Z by *E. coli*

The cytoplasmic domain and the extracellular domain of Semaphorin Z were separately expressed in the following manner.

Firstly, Semaphorin Z cDNA (SEQ ID NO: 1) was cleaved with restriction enzymes AatII and EcoRI, and electrophoresed on an agarose gel to prepare a fragment of 1.9 kb. The 1.9 kb fragment was ligated to an expression plasmid pRSETc (Invitrogen) cleaved at XhoI-EcoRI site together with an adapter DNA (5' TCGAGATCTGCAGCT-GACGT 3'(SEQ ID NO:14)/5' CAGCTGCAGATC 3'(SEQ ID NO:15)) to obtain a plasmid named pRSZinc for expression of the cytoplasmic domain.

Next, Semaphorin Z cDNA (SEQ ID NO: 1) was cleaved with BstBI and XhoI, and the 0.86 kbp fragment was separated and isolated by agarose gel electrophoresis. The fragment was ligated to pRSETc cleaved at XhoI-BstBI site using two adapters (5' TCGAGCTGTGACTGGTGTGGT-GACGGTTCCCG 3'(SEQ ID NO:16)/5' GGCCGCCAAG-GCTCACCACACCAGTCACAGC 3' (SEQ ID NO: 17) and 5'CCTGATAATAGTT 3'(SEQ ID NO:18)/5' CGAAC-TATTATCAGGACGT 3'(SEQ ID NO:19)) to obtain a plasmid, named rSZexII, for expression of the extracellular domain.

Figure 4:
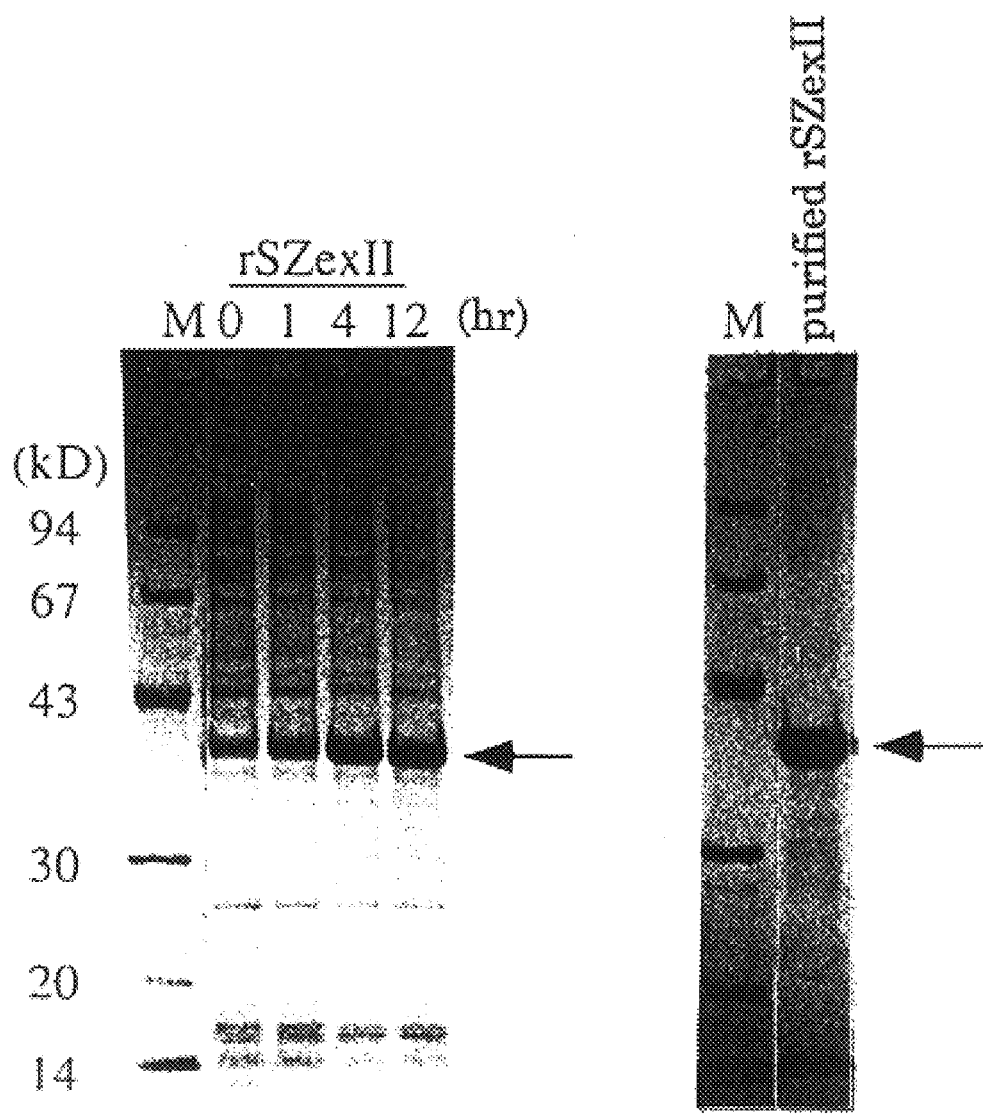
Figure 5:
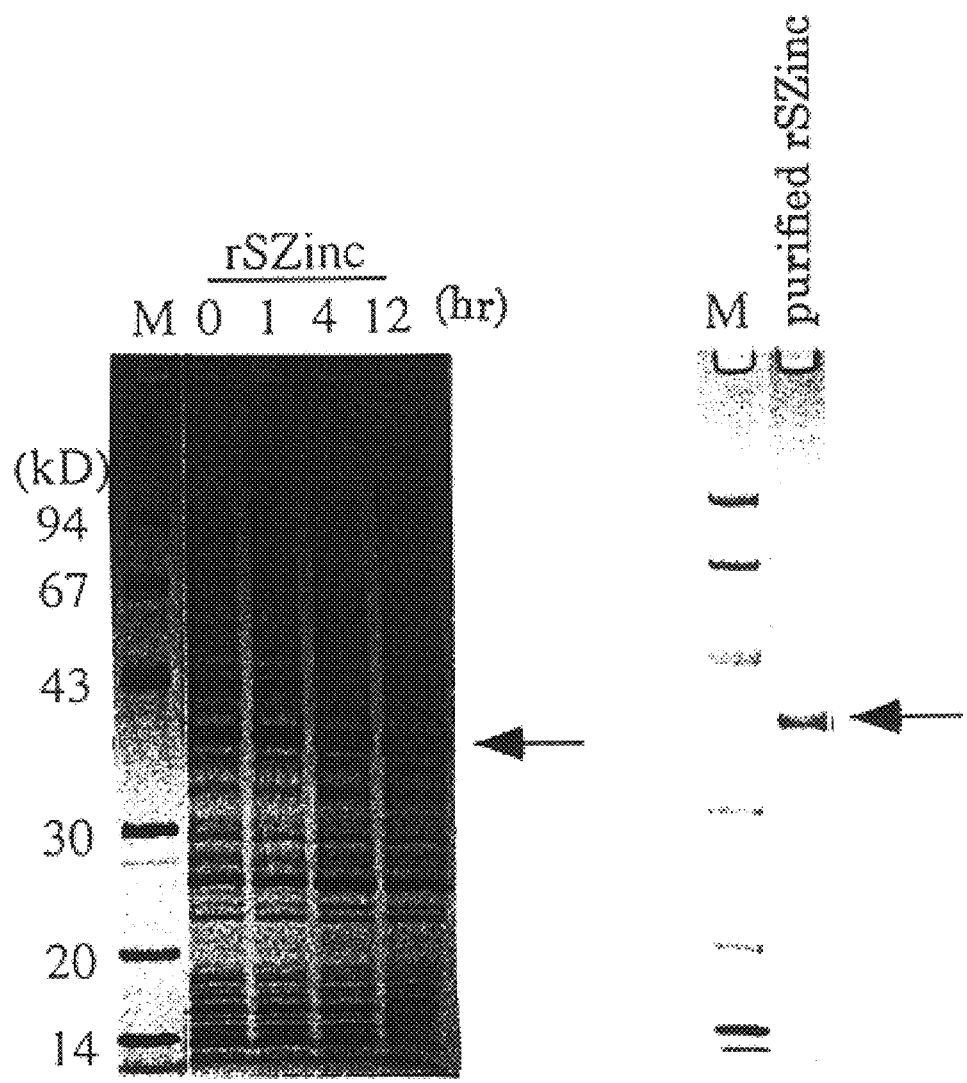

Using the plasmid pRSZinc or pRSZexII thus obtained, *E. coli*. BL21(DE3)pLysS (Stratagene) was transformed, and cultured overnight on a LB plate containing 50 μg/ml ampicillin to obtain a transformant. By analyzing the nucleotide sequence, it was confirmed that the transformant carry a plasmid having the desired structure. The transformant was cultured with shaking in LB broth containing 50 μg/ml ampicillin, and when OD$_{600}$ reached 0.5, IPTG was added at a final concentration of 1 mM, and further cultured for 12 hours. Subsequently, the culture medium was centrifuged at 5000 g for 15 min to harvest the cells. The whole proteins of the harvested cells were analyzed by SDS-PAGE, and it was confirmed on the basis of the molecular weights that the desired proteins, that is, rSZinc (the cytoplasmic domain of Semaphorin Z) and rSZexII (the extracellular domain of Semaphorin Z) have been produced. The results are shown in FIGS. 4 and 5.

Example 5

Purification of Semaphorin Z

The above-described rSZinc and rSZexII expressed in *E. coli* were affinity-purified using the affinity between the histidine tag located at the amino terminal of these proteins and a nickel-NTA resin. The procedure is described in detail in the protocols of Qiagen attached to the nickel-NTA resin (QIAexpressionist). Briefly, 5 ml of A solution (6M guanidine-HCl, 0.1 M sodium phosphate, 0.01 M Tris-HCl pH=8.0) was added to each 1 g of *E. coli* cells expressing rSZinc or rSZexII obtained by the method described in Example 4. The cells were suspended well in the solution, and stirred at room temperature for more than 1 hour to be solubilized. The solution was then mixed with a nickel-NTA resin pre-equilibrated with A solution, gently stirred at room temperature for more than 2 hours to allow the binding of the desired protein to the resin, and then the resin was packed into a column. The column was washed with 10 volumes of A solution, then with 5 volumes of B solution (8M urea, 0.1 M sodium phosphate, 0.01 M Tris-HCl pH=8.0), and further with 5 volumes of C solution (8M urea, 0.1 M sodium phosphate, 0.01 M Tris-HCl pH=6.3). The bound proteins were then eluted with 2 volumes of D solution (8 M urea, 0.1 M sodium phosphate, 0.01 M Tris-HCl pH=5.9), and further eluted with E solution (8M urea, 0.1 M sodium phosphate, 0.01 M Tris-HCl pH=4.5). During the elution, the eluate was collected in one column volume fractions, and subjected to SDS-PAGE to check the proteins eluted. The desired fractions were then concentrated, and stored at −20° C. until use.

The N-terminal amino acid sequence of the purified rSZinc and rSZexII thus obtained was determined to confirm that they were the desired proteins. The results of SDS-PAGE of these purified rSZinc and rSZexII are shown in FIGS. 4 and 5.

Example 6

Production of Anti-semaphorin Z Antibody

The purified rSZinc or rSZexII obtained in Example 5 was separated by SDS-PAGE (6% polyacrylamide gel), stained with CBB, and the desired band was excised. The excised gel block was cut into small pieces, and its aliquot corresponding to 0.4 mg protein was mixed with Freund's complete adjuvant. Using the mixture, a rabbit was then subcutaneously immunized. Subsequently, the rabbit was further subcutaneously immunized 3 times at intervals of 2 weeks with 0.2 mg of the protein mixed with Freund's incomplete adjuvant. One week after the last immunization, whole blood was collected from the rabbit. Purification was carried out by the conventional method using a protein A column, an rSZinc or rSZexII affinity column to obtain a purified polyclonal antibody.

Since the antibody has recognized Semaphorin Z of the present invention in Western blotting described below in Example 7, and the antibody pre-absorbed to the antigen, i.e., rSZinc or rSZexII, has failed to recognize Semaphorin Z, the antibody has proved to react specifically with Semaphorin Z.

Example 7

Expression of Semaphorin Z by Mammalian Cells

Semaphorin Z cDNA (SEQ ID NO: 1) was inserted into the EcoRI site of an expression vector for mammalian cell, pUCSRα, to obtain an expression plasmid pUCSRαSZ. COS 7 cells were transfected with pUCSRαSZ using DEAE-dextran method (F. M. Ausubel et al. ed, *Current Protocols in Molecular Biology*, John Wiley & Sons (1987)). After 48 hours, the cells were harvested using a cell scraper. The cells harvested were homogenized in the presence of A solution containing protease inhibitors (Hanks' physiological saline containing 10 mM HEPES pH 7.4, 1 mM EDTA, 50 μM leupeptin, 2 μM pepstatin, 0.5 mM PMSF, and 7.8 mTIU/ml aprotinin), and separated into the precipitate and the supernatant by high-speed centrifugation at 12000 g for 10 min. Since the supernatant still contained a considerable amount of the membrane fraction, it was further ultracentrifuged at 100000 g for 30 min, and the supernatant was recovered as a cytoplasmic fraction. The cytoplasmic fraction obtained was stored at −80° C. until use. The precipitate from the high-speed centrifugation were washed twice with A solution, suspended in 2 volumes of 2.25 M sucrose/PBS, and overlaid onto 2.25 M sucrose/PBS. After 0.8 M sucrose/PBS was further overlaid, it was centrifuged at 12000 g for 20 min. The membrane fraction was recovered from the lower interface, further washed twice, and stored at −80° C. until use.

Figure 6:
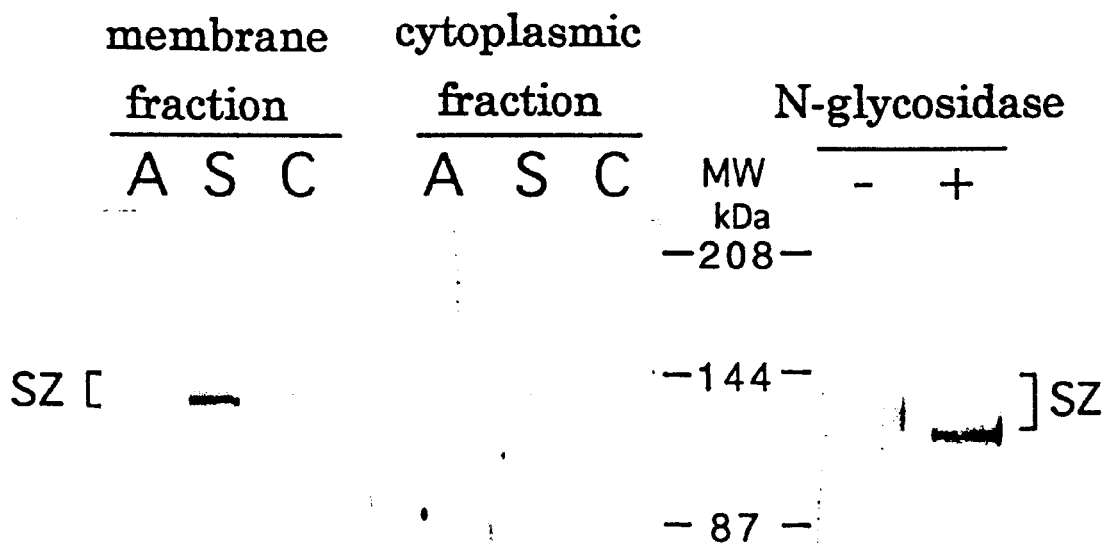

The cytoplasmic fraction and the membrane fraction obtained were subjected to SDS-PAGE (10%–20% gradient gel), and then to Western blotting by the method described below in Example 11 to confirm that Semaphorin Z of the present invention was expressed, and that it existed only in the membrane fraction. The result was shown in FIG. 6. As apparent from FIG. 6, Semaphorin Z expressed in the present Example had an apparent molecular weight of 110–150 kDa. When treated with N-glycosidase, the molecular weight of Semaphorin Z became about 110–130 kDa (FIG. 6), which is close to 93 kDa, the expected molecular weight calculated from the amino acid sequence.

The results described above demonstrated that Semaphorin Z of the present invention is a glycoprotein localized in the membrane. In the present Example, samples prepared in the same manner as described above from COS 7 cells which were mock-transfected, or transfected with antisense-Semaphorin Z expression plasmid pUCSRαSZ (−), were used as controls.

Example 8

Measurement of the Growth-cone Collapse Activity of Semaphorin Z

Semaphorin Z cDNA (SEQ ID NO: 1) was inserted into the EcoRI site of an expression vector for mammalian cells, pUCSRα, in the sense or antisense direction to obtain expression plasmids pUCSRαSZ(+) and pUCSRαSZ(−). COS 7 cells were transfected with these expression plasmids by the DEAE-dextran method described in Example 7, and after 48 hours, harvested using a cell scraper. The cells harvested were homogenized (20 strokes) using a Dounce homogenizer (tight type) in the presence of protease inhibitors as described in Example 7. The cell homogenate was obtained by centrifuging the mixture at 12000 g for 5 min to remove the precipitate. The protein concentration of this homogenate was measured by the BCA method (Pierce).

The dorsal root ganglion (DRG) was disected from chicken embryonic-day 8 embryo (E8 embryo), incubated at 37° C. for 13 hours in F12 medium/10% FCS containing 20 ng/ml NGF or NT-3 in the presence of 5% $CO_2$ in a chamber slide coated with poly-L-lysine-laminin, and subjected to a measurement of the growth-cone collapse activity. The method of measuring the growth-cone collapse activity is described in detail in *Neuron*, 2, 11–20 (1990), *Neuron*, 2, 21–29 (1990), *Neuron*, 2, 31–37 (1990). Briefly, the measurement was carried out according to the following procedures: Firstly, the above cell homogenate, 1/4 volumes relative to the medium, was added to the chamber containing the cultured dorsal root ganglion, incubated at 37° C. for 1 hour, and then fixed by adding 1% glutaraldehyde/PBS for 15 min. After washing once with PBS, a specimen was prepared using a mounting agent (MountQuick, Daido Sangyo). After confirming that the mounting agent has hardened, the number of collapsed growth corns were counted under a microscope. For each sample, four chambers each containing 2 dorsal root ganglions were incubated, and the average and deviation were calculated. As described in *Neuron*, 2, 21–29 (1990), evaluation of collapse was done on about 50 neurites having the longest length for each dorsal root ganglion.

As shown in FIG. 7, the extract of COS cell expressing Semaphorin Z (semaZ) had significantly higher growth-cone collapse activities on NGF or NT-3 dependent DRG neural growth cone ($p<0.001$ and $p<0.01$, respectively).

Example 9

Construction of Recombinant Adenovirus Expressing Semaphorin Z

The method of preparing adenoviruses are described in detail in *Jikken-Igaku-Zokan* vol. 12, #15 (1994). Briefly, a recombinant adenovirus expressing Semaphorin Z cDNA in the antisense direction was prepared by the following method. The EcoRI-MluI fragment of Semaphorin Z CDNA (SEQ ID NO: 1) was prepared, blunted by DNA polymerase Klenow fragment, and ligated to an adenovirus cassette cosmid pAx1CAwt cleaved with SwaI. The construct was in vitro packaged, and transfected to *E. coli* DH5α. Cosmid DNA was prepared from the transformant thus obtained, and it was confirmed from its restriction enzyme cleavage pattern that Semaphorin Z cDNA has been inserted in the antisense direction. This cosmid was designated pAx1CASemaZ-R. In addition, a Semaphorin Z expression cosmid was prepared in the same manner, and designated pAx1CASemaZ-L. The pAx1CASemaZ-R was co-transfected into 293 cells together with wild-type adenovirus type-5 DNA by the calcium phosphate method. The next day the 293 cells were mixed with untreated 293 cells, re-plated on a 96-well plate, and their cytopathic states were observed everyday. The cells began to degenerate after 10 days. After additional 3–5 days, clones corresponding to the wells in which all the cells were lysed were selected for the next infection. Using the selected clones, 293 cells placed in 25 cm² flasks were infected, and incubated until all the cells were lysed. The culture for each cell was separately collected, and its aliquot was used to prepare the DNA in order to confirm that Semaphorin Z cDNA has been inserted in the antisense direction. With a clone having the insert in the correct direction, the infection of 293 cells was repeated twice to amplify the virus. The amplified virus was then purified, and stored at –80° C. in 10% glycerol/PBS(–) until use.

Example 10

Expression of Antisense-Semaphorin Z7 mRNA by a Recombinant Adenovirus $2\times10^6$ COS 7 cells were cultured sub-confluently, and the medium was removed. To the cells, 0.3 ml of the recombinant adenovirus (moi=10) was added, and the mixture was allowed to stand for 1 hour, and then 4.7 ml of medium was added hereto. After incubating for 2 days, the total RNA was extracted using ISOGEN (Nippon Gene). Ten μg of the RNA was used for Northern blotting in the same manner as described in Example 3, and the filter obtained was hybridized with an RNA probe specifically labeled on the sense- or antisense-strand of Semaphorin cDNA with $^{32}$P. As shown in FIG. 8, a strong signal was observed only when the sense probe was used, confirming that the recombinant adenovirus Ax1CAsemaZ-R highly and selectively expresses the antisense-Semaphorin Z mRNA. Datailed for the preparation of the RNA probe used herein can be found in *Molecular Cloning* 2nd Ed. (Cold Spring Harbor Laboratory Press, 1989). Briefly, however, the sense probe was, for example, synthesized in the following manner. Firstly, 2 primers (5'-CAGGAACACGAACCACAC-3' (SEQ ID NO: 12) and 5'-GTATGCAAGAATGATGTG-3' (SEQ ID NO: 13)) were used in a PCR reaction with rat Semaphorin Z cDNA as a template to obtain a fragment of 775 bp. This DNA fragment was cloned into pCRII (Invitrogen), and its direction of insertion was confirmed. This plasmid was cleaved with SpeI, and used as a template for preparing the probe. The labeling reaction was carried out at 37° C. for 1 hour in a total volume of 20 μl containing 0.5 μg of the template, 2 μl of 10×buffer, 4 μl of 2.5 mM rATP, rGTP, and rCTP, 2.4 μl of 100 μM rUTP, 5 μl of [$\alpha^{32}$P] rUTP, 1 μl (20 units) of T7 polymerase, 1 μl of RNase inhibitor, and distilled water. After adding 2 μl of DNase, the reaction was further continued for 15 min. The antisense probe was prepared in the same manner as before with the exceptions that the template was cleaved with EcoRV instead of SpeI, and that SP6 polymerase was substituted for T7 polymerase.

Example 11

Inhibition of Semaphorin Z Expression by a Recombinant Adenovirus $1\times10^6$ COS 7 cells were plated on a collagen (type I)-coated cell culture flask having a culture area of 25 cm² (Sumitomo Bakelite), and incubated for about one day in 5 ml of medium (DMEM+10% FCS) at 37° C. under 5% $CO_2$. The medium was then changed to 0.3 ml medium containing $2\times10^8$ pfu of a recombinant adenovirus (an antisense-Semaphorin Z or a control virus having no Semaphorin Z gene), and the cells were further incubated for 1 hour, allowing the cells to be infected by the adenovirus. During the infection, the flask was shaken at intervals of about 15 min in-order to avoid drying of the cells. Then, 4.7 ml of the culture medium was added, further incubated for one day, and 3 μg of the Semaphorin Z expression plasmid (pAx1CASemaZ-L) was introduced into the cells using Transfectam (Bio Sepra Inc.). A DNA solution containing the expression plasmid was prepared according to the attached protocol, and the DNA solution was contacted with the cells for 4 hours. At 12 and 24 hours after the introduction of the expression plasmid, the cells were harvested in the following manner. The cells were detached in the presence of medium using a cell scraper, collected by centrifugation (1000 rpm, 5 min, 4° C.), washed with PBS, and then suspended in 100 μl of a lysis buffer (Hanks' physiological saline containing 10 mM HEPES pH 7.4, 1 mM EDTA, 50 μM leupeptin, 2 μM pepstatin, 0.08 TIU/ml aprotinin, and 0.5 mM PMSF). Then, the cells were lysed by freeze-thawing, and separated into a soluble fraction and an insoluble fraction. The insoluble fraction was suspended in a denaturing solution (100 mM Tris-HCl pH 6.8, 2% SDS, 5% 2-mercaptoethanol), denatured and solubilized by heading at 100° C. for 10 min. The relative amounts of protein among samples were calculated by measuring the absorbance of the samples at 280 nm, and used in the following Western blot analysis. An aliquot containing a predetermined amount of protein was removed from each sample, mixed with an equal volume of 1×SDS-PAGE sample buffer (0.0625 M Tris-HCl pH6.8, 2% SDS, 5% 2-mercaptoethanol, 10% glycerol), and heated at 100° C. for 5 min. These protein samples were fractionated by SDS-PAGE (10% acrylamide), and then electrophoretically transferred (100V, 1 hour, in 25 mM Tris-HCl, 192 mM glycine, and 20% methanol) onto Immobilon filter (Millipore). After shaking for 1 hour in a blocking solution (2% skim milk, 1% BSA) to avoid any non-specific adsorption of antibody, the filter was placed in PBS containing 1/100 volume of the anti-Semaphorin Z antibody obtained in Example 6 as a primary antibody and 0.1% BSA, and allowed to stand overnight at 4° C. The next day the excessive antibody was washed off with PBS containing 0.05% Tween 20 (5 min, 3 times), and then shaken for 1 hour in PBS containing 1/1000 volume of an alkaline phosphatase-labeled anti-rabbit IgG antibody (BIOSORUCE) as a secondary antibody and 0.1% BSA. The filter was then washed as described above, and a developing solution (0.3 mg/ml NBT, 0.15 mg/ml BCIP, 100 mM Tris-HCl pH 9.5, 0.5 mM $MgCl_2$) was added. When a band of interest was detected, the solution was replaced with distilled water to stop the developing reaction.

As shown in FIG. 9, the expression of Semaphorin Z protein was observed 24 hours after the introduction of the expression plasmid for the cells infected with the control-adenovirus, but not for the cells infected with the antisense-adenovirus. Thus, the expression of Semaphorin Z protein was inhibited by the infection of the antisense-adenovirus.

Reference Example 1

Identification of the Site Essential to the Semaphorin Activity Using Semaphorin III PCR was conducted on the basis of the sequence information on Semaphorin III described in *Neuron*, 14, 941–948 (1995), and the structural gene of Semaphorin III was inserted into an expression plasmid pUCSRα. The expression plasmid was then introduced into COS 7 cell by the DEAE-dextran method. After 2 days, the Semaphorin III activity contained in the culture supernatant was determined by a method similar to that described in *Cell*, 75, 217–227 (1993), using the growth-cone collapse activity on chicken dorsal root ganglionic neuron as an indicator. As a result, one clone which did not exhibit any activity was found. The nucleotide sequencing of that clone revealed that aspartic acid at position 198 was substituted by glycine. When compared with other known animal Semaphorins, the regions before and after the position 198 were not markedly conserved, although the position corresponding to that aspartic acid was highly conserved among Semaphorins with a few exceptions in which glutamic acid was located at that position. This suggested that the aspartic acid is essential to expression of the activity. The gene was then subjected to a site-directed mutagenesis by a conventional method to replace the glycine with aspartic acid. Since this mutagenesis restored the strong collapse activity, it was confirmed that all the regions in the expression plasmid normally function except for that position. In conclusion, the aspartic acid at position 198 of Semaphorin III appears essential to expression of the Semaphorin function. The amino acid residues corresponding to the aspartic acid are the aspartic acid at position 204 in the amino acid sequence of rat Semaphorin Z shown in SEQ ID NO: 2, and the aspartic acid at position 203 in the amino acid sequence of human Semaphorin Z shown in SEQ ID NO: 4.

Reference Example 2

Tissue-specific Gene Expression of Semaphorin III Determined by Northern Analysis To determine the expression distribution of Semaphorin III gene in mouse tissues, RNAs were prepared from various adult mouse tissues, and subjected to Northern analysis. The procedures for preparation, blotting, and hybridization of RNA were as those described in Example 1. As a probe, the 560 bp MspI fragment of mouse Semaphorin III DNA described in Reference example 1 was used. As a result, it was demonstrated as shown in FIG. 10 that the expression of Semaphorin III in adult is very high in lung which is a peripheral organ, while it is rather low in CNS.

EFFECTS OF THE INVENTION

The present invention may provide a gene for novel Semaphorin Z inhibiting neurite outgrowth, another Semaphorin gene hybridizing to said gene, DNA or RNA having a sequence complementary to those genes, a protein obtained by expressing Semaphorin Z gene, a partial peptide of Semaphorin Z, a modified protein obtained by expressing a modified gene, and antibodies against them, as well as a screening system for Semaphorin Z inhibitor using Semaphorin Z, a Semaphorin Z inhibitor isolated from said system, and so on. By using such materials or systems, pharmaceutical agents principally having a CNS-neuron regeneration effect, or reagents useful in the medical and biological research on Semaphorin Z are provided.

What is claimed is:

1. An isolated nucleic acid comprising a polynucleotide having nucleotide sequence selected from the group consisting of:
   (a) the nucleotide sequence of SEQ ID NO:1;
   (b) the nucleotide sequence of SEQ ID NO:3;
   (c) the nucleotide sequence of SEQ ID NO:1 from nucleotide 19 to nucleotide 2682;
   (d) the nucleotide sequence of SEQ ID NO:3 from nucleotide 39 to nucleotide 2702;
   (e) a nucleotide sequence encoding the amino acid sequence of SEQ ID NO:2; and
   (f) a nucleotide sequence encoding the amino acid sequence of SEQ ID NO:4.

2. An isolated nucleic acid molecule comprising a polynucleotide that specifically hybridizes with a polynucleotide having a nucleotide sequence selected from the group consisting of:
   (a) the complement of the nucleotide sequence of SEQ ID NO:1; and
   (b) the complement of the nucleotide sequence of SEQ ID NO:3;
      under hybridization conditions of a buffer comprising 45% (v/v) formamide, 5×SSPE, at 42° C., and washing conditions after hybridization of a buffer comprising 2×SSPE at 42° C.,
   wherein said isolated nucleic acid molecule encodes a protein having the biological activity of collapsing growth cones of dorsal root ganglion cells.

3. An isolated pdlynucleotide consisting of at least 18 contiguous nucleotides of the nucleotide sequence of SEQ ID NO:1 from nucleotide 19 to nucleotide 2682 or of the nucleotide sequence of SEQ ID NO:3 from nucleotide 39 to nucleotide 2702, with the exception of a polynucleotide consisting of at least 18 contiguous nucleotides completely complementary to the nucleotide sequence disclosed in Genebank Accession NO:T08532 (SEQ ID NO:20).

4. An isolated polynucleotide which is complementary to the polynucleotide of claim 3.

5. An expression plasmid comprising the DNA of claim 1 or 2.

6. A host cell comprising the expression plasmid of claim 5.

7. A process for producing a recombinant protein, comprising:
   culturing the host cell of claim 6 under conditions sufficient for the production of said protein; and
   recovering said protein.

* * * * *